(12) United States Patent
Hao et al.

(10) Patent No.: US 12,706,219 B2
(45) Date of Patent: Aug. 11, 2026

(54) SYSTEMS AND METHODS FOR SCAN PREPARATION

(71) Applicant: SHANGHAI UNITED IMAGING HEALTHCARE CO., LTD., Shanghai (CN)

(72) Inventors: Xin Hao, Shanghai (CN); Yuan Bao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 51 days.

(21) Appl. No.: 18/642,766

(22) Filed: Apr. 22, 2024

(65) Prior Publication Data

US 2024/0312638 A1 Sep. 19, 2024

Related U.S. Application Data

(63) Continuation-in-part of application No. 16/997,005, filed on Aug. 19, 2020, now Pat. No. 11,967,429.

(30) Foreign Application Priority Data

Aug. 19, 2019 (CN) ........................ 201910764364.X

(51) Int. Cl.
*G16H 50/50* (2018.01)
*G16H 30/40* (2018.01)

(52) U.S. Cl.
CPC ............. *G16H 50/50* (2018.01); *G16H 30/40* (2018.01)

(58) Field of Classification Search
CPC ......... G16H 50/50; G16H 30/40; G16H 30/20
(Continued)

(56) References Cited

U.S. PATENT DOCUMENTS 6,154,516 A 11/2000 Heuscher et al.
2003/0161435 A1 8/2003 Ozaki
(Continued)

FOREIGN PATENT DOCUMENTS

CN 1927123 A 3/2007
CN 103083035 A 5/2013
(Continued)

OTHER PUBLICATIONS

H. R. Roth et al., Hierarchical 3D Fully Convolutional Networks for Multi-organ Segmentation, Cornell University, 2017, 11 pages.
(Continued)

*Primary Examiner* — Reginald R Reyes
(74) *Attorney, Agent, or Firm* — METIS IP LLC

(57) ABSTRACT

Systems and methods for scan preparation are provided. The systems may obtain a first parameter set of a subject to be scanned by a medical device acquired before a scan is performed on the subject. The first parameter set may relate to a physiological motion of the subject acquired before the scan is performed on the subject. The systems may predict, based on the first parameter set and an estimation model, a second parameter set of the subject. The second parameter set may relate to the physiological motion of the subject. The systems may determine at least one scan parameter for the scan based at least in part on the second parameter set. The systems may cause the medical device to perform the scan on the subject based on the at least one scan parameter.

19 Claims, 9 Drawing Sheets

(58) Field of Classification Search
USPC .............................................................. 378/4
See application file for complete search history.

(56) References Cited

U.S. PATENT DOCUMENTS

2003/0208106 A1 11/2003 Anderson et al.
2009/0060386 A1 3/2009 Cooper et al.
2009/0168951 A1 7/2009 Yan
2010/0183206 A1* 7/2010 Carlsen .................. A61B 6/488 382/128
2010/0208863 A1 8/2010 Heuscher et al.
2010/0217139 A1 8/2010 Pinter et al.
2010/0249574 A1 9/2010 Miyazaki
2011/0208046 A1 8/2011 Gonzalez Molezzi et al.
2012/0213326 A1 8/2012 Walker et al.
2013/0274601 A1 10/2013 Akiyama et al.
2014/0185780 A1 7/2014 Zhao et al.
2014/0206991 A1 7/2014 Korporaal
2015/0038839 A1 2/2015 Schaefer et al.
2015/0381985 A1 12/2015 Oh et al.
2016/0042012 A1 2/2016 Lou et al.
2016/0210602 A1 7/2016 Siddique et al.
2017/0209111 A1 7/2017 Choi et al.
2017/0281983 A1* 10/2017 Marquet .............. A61B 5/7285
2018/0289340 A1 10/2018 Trindade Rodrigues et al.
2018/0338727 A1 11/2018 Mukhopadhyay et al.
2018/0374216 A1 12/2018 Hu
2019/0005199 A1 1/2019 Rowley Grant et al.
2019/0142492 A1* 5/2019 Kollmann .............. A61B 18/02 606/21
2019/0143145 A1* 5/2019 Laurence, Jr. ......... A61B 34/10 600/1
2020/0093386 A1 3/2020 Biswas et al.
2021/0378540 A1* 12/2021 Arad ...................... A61B 5/053

FOREIGN PATENT DOCUMENTS

CN 108814580 A 11/2018
CN 108926338 A 12/2018
CN 109409053 A 3/2019
CN 109686433 A 4/2019
CN 110420019 A 11/2019
CN 110811623 A 2/2020
CN 111128345 A 5/2020
EP 1350539 A1 10/2003
WO 2005067383 A2 7/2005

OTHER PUBLICATIONS

Özgün Çiçek et al., 3D U-Net: Learning Dense Volumetric Segmentation from Sparse Annotation, MICCAI, 2016, 8 pages.
Di, Jie, Comparative Study Between 64-slice Spiral Computed Tomography and Coronary Artery Angiography for Detecting Coronary Artery Disease in Patients with Tachycardia or Arrhythmia, China Masters' Theses Full-text Database, 2011, 63 pages.
First Office Action in Chinese Application No. 201910764364.X mailed on Sep. 3, 2021, 28 pages.

* cited by examiner

Figure 6:
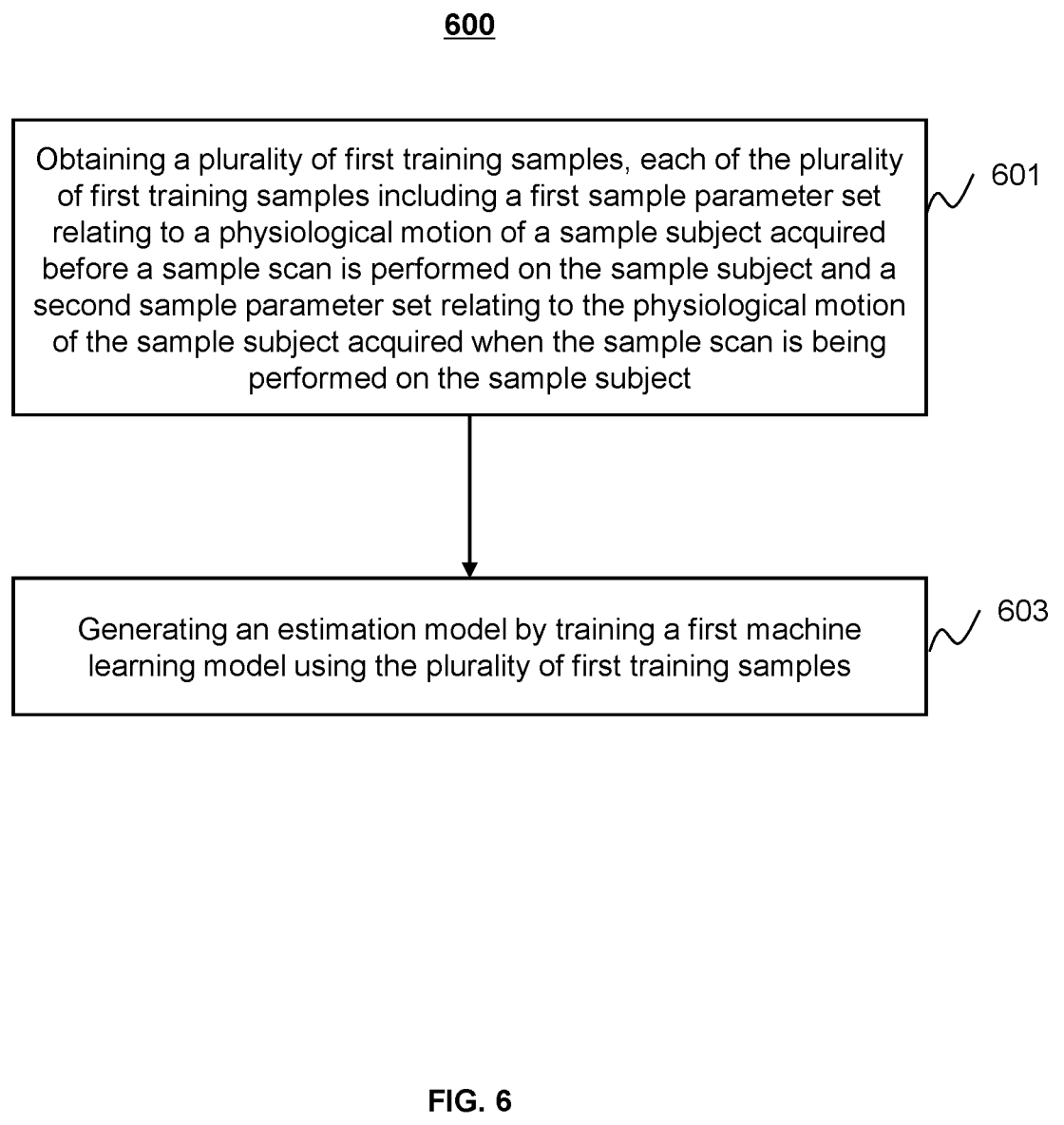

600

Obtaining a plurality of first training samples, each of the plurality of first training samples including a first sample parameter set relating to a physiological motion of a sample subject acquired before a sample scan is performed on the sample subject and a second sample parameter set relating to the physiological motion of the sample subject acquired when the sample scan is being performed on the sample subject

601

Generating an estimation model by training a first machine learning model using the plurality of first training samples

SYSTEMS AND METHODS FOR SCAN PREPARATION

CROSS-REFERENCE TO RELATED APPLICATIONS

This application is a continuation-in-part application of U.S. application Ser. No. 16/997,005, filed on Aug. 19, 2020, which claims priority of Chinese Patent Application No. 201910764364.X, filed on Aug. 19, 2019, the contents of which are hereby incorporated by reference.

TECHNICAL FIELD

The disclosure generally relates to medical technology, and more particularly relates to systems and methods for scan preparation.

BACKGROUND

With the development of medical technology, the time resolution and image quality of medical scanning devices become higher and higher. In some occasions, a patient needs to be injected with a contrast agent during a scan, which may affect physiological motion (e.g., heart rate, blood pressure) of the subject. Currently, during scan preparation, the effect of injection of the contrast agent on the physiological motion cannot be simulated; moreover, it is difficult to optimize or personalize scan parameters to account for differences of different patients. In some embodiments, the scan parameters may be set manually by a user of the medical scanning device. In such cases, the user needs to have extensive experience and/or be familiar with the medical scanning device. In some embodiments, a scan range and/or scan times may be increased to improve the chances for a successful scan of a patient, thereby resulting in that the patient is exposed to unnecessary radiation. Therefore, it is desired to provide systems and methods for scan preparation in which scanning parameters recommendation is automated and therefore achieved more efficiently and accurately, thereby reducing or removing unnecessary radiation dose during a scan.

SUMMARY

In one aspect of the preset disclosure, a system for scan preparation is provided. The system may include at least one storage device including a set of instructions and at least one processor configured to communicate with the at least one storage device. When executing the set of instructions, the at least one processor may be configured to direct the system to perform following operations. The system may obtain a first parameter set of a subject to be scanned by a medical device acquired before a scan is performed on the subject. The first parameter set may relate to a physiological motion of the subject acquired before the scan is performed on the subject. The system may predict, based on the first parameter set and an estimation model, a second parameter set of the subject. The second parameter set may relate to the physiological motion of the subject. The system may determine at least one scan parameter for the scan based at least in part on the second parameter set. The system may cause the medical device to perform the scan on the subject based on the at least one scan parameter.

In some embodiments, the first parameter set may include at least one of a first parameter sub-set acquired during a first time period and a second parameter sub-set acquired during a second time period different from the first time period.

In some embodiments, the subject may be not undergoing any scan during the first time period, and the subject may be undergoing a simulated scan during the second time period.

In some embodiments, the predicting, based on the first parameter set and an estimation model, a second parameter set of the subject may include predicting the second parameter set of the subject by inputting the first parameter set to the estimation model.

In some embodiments, the determining at least one scan parameter for the scan based at least in part on the second parameter set may include obtaining a recommendation model; obtaining health information of the subject; and determining the at least one scan parameter for the scan by inputting the second parameter set and the health information of the subject into the recommendation model.

In some embodiments, the inputting the second parameter set and the health information of the subject into the recommendation model may include preprocessing the health information of the subject; and inputting the second parameter set and the preprocessed information of the subject into the recommendation model.

In some embodiments, the preprocessing the health information of the subject may include performing a word segmentation operation on the health information of the subject.

In some embodiments, the at least one processor may further be configured to direct the system to perform the operations including causing at least a portion of the at least one scan parameter to be presented to a user.

In some embodiments, the at least one processor may further be configured to direct the system to perform the operations including receiving a user input. The causing the medical device to perform the scan on the subject based on the at least one scan parameter may include causing the medical device to perform the scan on the subject based on the at least one scan parameter and the user input.

In some embodiments, the causing the medical device to perform the scan on the subject based on the at least one scan parameter and the user input may include adjusting the at least one scan parameter based on the user input, and causing the medical device to perform the scan on the subject based on the adjusted at least one scan parameter.

In some embodiments, the at least one processor may further be configured to direct the system to perform the operations including adjusting the at least one scan parameter until an image generated by the scan performed on the subject based on the adjusted at least one scan parameter satisfies a preset condition.

In some embodiments, the at least one processor may further be configured to direct the system to perform the operations including updating a recommendation model based at least in part on the second parameter set, health information of the subject, and the adjusted at least one scan parameter, the recommendation model being configured to determine the at least one scan parameter for the scan.

In some embodiments, the at least one processor may further be configured to direct the system to perform the operations including obtaining a third parameter set of the subject acquired when the scan is being performed on the subject; determining a difference between the third parameter set of the subject and the second parameter set of the subject; and determining whether to update the estimation model based at least in part on the difference.

In some embodiments, the scan may be associated with a cardiac angiography.

In some embodiments, the physiological motion may include cardiac motion of the subject, and the first parameter set or the second parameter set may relate to a heart rate of the subject.

In some embodiments, the at least one scan parameter may include at least one of a count of cardiac cycles during the scan, a first phase range during the scan, a pitch of the medical device, a second phase range relating to a radiation dose control, exposure time, or a dose range relating to the radiation dose control.

In some embodiments, the estimation model may be generated by a processing including obtaining a plurality of first training samples and generating the estimation model by training a first machine learning model using the first plurality of training samples. Each of the plurality of first training samples may include a first sample parameter set relating to the physiological motion of a sample subject acquired before a sample scan is performed on the sample subject and a second sample parameter set relating to the physiological motion of the sample subject acquired when the sample scan is being performed on the sample subject.

In some embodiments, the recommendation model may be generated by a processing including obtaining a plurality of second training samples and generating the recommendation model by training a second machine learning model using the plurality of second training samples. Each of the plurality of second training samples may include a third sample parameter set relating to the physiological motion of a sample subject when a sample scan is being performed on the sample subject, sample health information of the sample subject, and at least one sample scan parameter based on which the sample scan is performed.

In another aspect of the present disclosure, a method for scan preparation is provided. The method may be implemented on a computing device including at least one processor and at least one storage device. The method may include obtaining a first parameter set of a subject to be scanned by a medical device acquired before a scan is performed on the subject. The first parameter set may relate to a physiological motion of the subject acquired before the scan is performed on the subject. The method may also include predicting, based on the first parameter set and an estimation model, a second parameter set of the subject. The second parameter set may relate to the physiological motion of the subject. The method may also include determining at least one scan parameter for the scan based at least in part on the second parameter set. The method may further include causing the medical device to perform the scan on the subject based on the at least one scan parameter.

In another aspect of the present disclosure, a non-transitory computer readable medium is provided. The non-transitory computer readable medium may include executable instructions that, when executed by at least one processor, direct the at least one processor to perform a method for scan preparation. The method may include obtaining a first parameter set of a subject to be scanned by a medical device acquired before a scan is performed on the subject. The first parameter set may relate to a physiological motion of the subject acquired before the scan is performed on the subject. The method may also include predicting, based on the first parameter set and an estimation model, a second parameter set of the subject. The second parameter set may relate to the physiological motion of the subject. The method may also include determining at least one scan parameter for the scan based at least in part on the second parameter set. The method may further include causing the medical device to perform the scan on the subject based on the at least one scan parameter.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for generating an estimation model according to some embodiments of the present disclosure;

FIG. 8 is a flowchart illustrating an exemplary process for generating a recommendation model according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
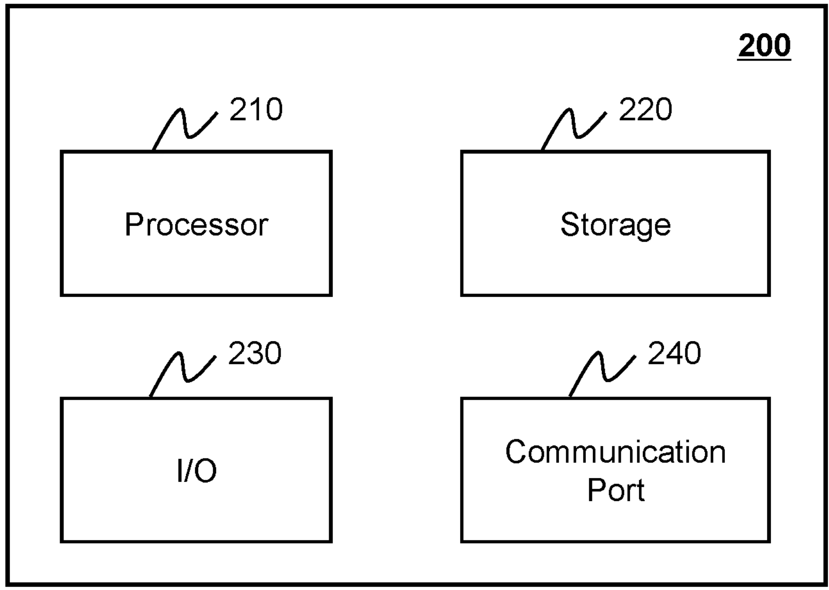
FIG. 2 is a schematic diagram illustrating hardware and/or software components of an exemplary computing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data) and/or images of various forms, including a two-dimensional (2D) image, a three-dimensional (3D) image, a four-dimensional (4D) image, etc. The term "pixel" and "voxel" in the present disclosure are used interchangeably to refer to an element of an image.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "imaging modality" or "modality" as used herein broadly refers to an imaging method or technology that gathers, generates, processes, and/or analyzes imaging information of a subject. The subject may include a biological subject (e.g., a human, an animal), a non-biological subject (e.g., a phantom), etc. In some embodiments, the subject may include a specific part, organ, and/or tissue of the subject. For example, the subject may include head, brain, neck, body, shoulder, arm, thorax, cardiac, stomach, blood vessel, soft tissue, knee, feet, or the like, or any combination thereof. The term "object" or "subject" are used interchangeably.

An aspect of the present disclosure relates to systems and methods for scan preparation for a scan using a radiation-based medical device. The systems and methods may obtain a first parameter set of a subject to be scanned by a medical device acquired before a scan is performed on the subject. The first parameter set may relate to a physiological motion of the subject before the scan is performed on the subject. The systems and methods may predict, based on the first parameter set and an estimation model, a second parameter set of the subject (e.g., on an assumption that the scan is performed on the subject). The second parameter set may relate to the physiological motion of the subject (e.g., on the assumption that the scan is performed on the subject). The systems and methods may determine at least one scan parameter for the scan based at least in part on the second parameter set. The second parameter set may further be used to recommend the at least one scan parameter for a user of the medical device using a recommendation model. The systems and methods may cause the medical device to perform the scan on the subject based on the at least one scan parameter.

According to some embodiments of the present disclosure, the determination of various parameters including, e.g., the second parameter set of the subject, the scan parameters, may be automated using an estimation model and/or a recommendation model. The automated determination of various parameters may improve the efficiency of scan preparation, and reduce or remove dependence on user experience and/or inter-user variation in the parameter determination process. Either or both of the estimation model and the recommendation model may be trained based on data from a plurality of sample subjects, which can better account for differences in different subjects to be scanned, including the differences in health conditions, the physicological motion (e.g., the heart rate), etc., of different subjects, thereby improving the accuracy of parameters to be used in a scan, reducing the radiation dosage, shortening the scan time, and improving scan success rates. Further, data generated during new scans may be used to continuously optimize the estimation model and/or the recommendation model, thereby further improving the efficiency and/or accuracy of the parameters determined using the estimation model and/or the recommendation model.

Figure 1:
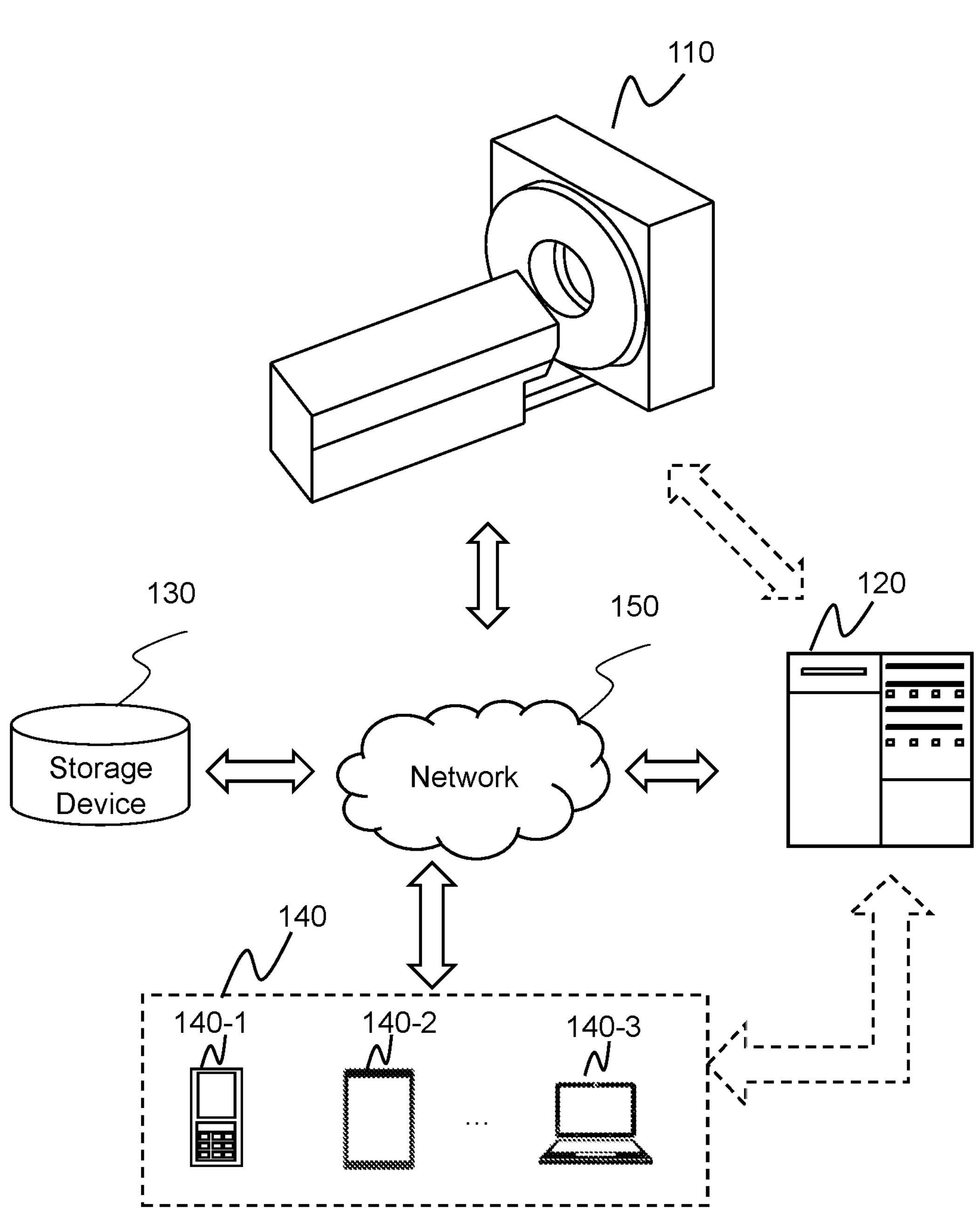
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. In some embodiments, the imaging system may be configured for non-invasive biomedical imaging (e.g., cardiac angiography), such as for disease diagnostic, treatment, and/or research purposes. In some embodiments, the imaging system may include a single modality imaging system and/or a multi-modality imaging system. The single modality imaging system may include, for example, an X-ray imaging system, a computed tomography (CT) system (e.g., a spiral CT system, a cone-beam CT system, etc.), a single photon emission computed tomography (SPECT) system, a digital radiography (DR) system, or the like, or any combination thereof. The multi-modality imaging system may include, for example, a positron emission tomography-CT (PET-CT) system, an X-ray imaging-magnetic resonance imaging (X-ray-MRI) system, a SPECT-MRI system, a CT guided radiotherapy system, etc. It should be noted that the imaging system described below is merely provided for illustration purposes, and not intended to limit the scope of the present disclosure.

In some embodiments, the imaging system 100 may include modules and/or components for performing imaging and/or related analysis. Merely by way of example, as illustrated in FIG. 1, the imaging system 100 may include a medical imaging device 110, a processing device 120, a storage device 130, one or more terminals 140, and a network 150. The components in the imaging system 100 may be connected in various ways. Merely by way of example, the medical device 110 may be connected to the processing device 120 through the network 150 or directly as illustrated in FIG. 1. As another example, the terminal(s) 140 may be connected to the processing device 120 via the network 150 or directly as illustrated in FIG. 1. For brevity, the medical imaging device 110 is also referred to as medical device 110.

The medical device 110 may be configured to acquire imaging data relating to a subject. The imaging data relating to a subject may include an image (e.g., an image slice), projection data, or a combination thereof. In some embodiments, the imaging data may be two-dimensional (2D) imaging data, three-dimensional (3D) imaging data, four-dimensional (4D) imaging data, or the like, or any combination thereof. In some embodiments, the medical device 110 may include a CT device (e.g., a CT device), an X-ray imaging device, a DR device, a SPECT device, a PET-CT device, an X-ray-MRI device, a SPECT-MRI device, a CT guided radiotherapy device. The following descriptions are provided with reference to the medical device 110 being a CT device. It is understood that this is for illustration purposes and not intended to be limiting. In some embodiments, the imaging device 110 may include a radiation source, a detector, a gantry, a table, etc. The radiation source and the detector may be mounted on the gantry. The subject may be placed on the table and moved to an imaging region of the imaging device. The radiation source may include a tube configured to emit radioactive rays (e.g., X rays) traveling toward the subject. The detector may detect radiation (e.g., X-rays) emitted from the imaging region of the imaging device 110. In some embodiments, the detector may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The processing device 120 may process data and/or information obtained from the medical device 110, the terminal(s) 140, and/or the storage device 130. For example, the processing device 120 may predict a second parameter set relating to a physiological motion of a subject to be scanned based on a first parameter set relating to the physiological motion of the subject and an estimation model. As another example, the processing device 120 may determine at least one scan parameter for a scan based at least in part on the second parameter set and a recommendation model. As still an example, the processing device 120 may train the estimation model using a plurality of first training samples. Each of the plurality of first training samples may include a first sample parameter set relating to the physiological motion of a sample subject acquired before a sample scan is performed on the sample subject and a second sample parameter set relating to the physiological motion of the sample subject acquired when the sample scan is being performed on the sample subject. As a further example, the processing device 120 may train the recommendation model using a plurality of second training samples. Each of the plurality of second training samples may include a third sample parameter set relating to the physiological motion of a sample subject when a sample scan is being performed on the sample subject, sample health information of the sample subject, and at least one sample scan parameter based on which the sample scan is performed.

In some embodiments, the generation and/or updating of the estimation model and/or the recommendation model may be performed on a processing device, while the application of the estimation model and/or the recommendation model may be performed on a different processing device. In some embodiments, the generation and/or updating of the estimation model and/or the recommendation model may be performed on a processing device of a system different from the imaging system 100 or a server different from a server including the processing device 120 on which the application of the estimation model and/or the recommendation model is/are performed. For instance, the generation of the estimation model and/or the recommendation model may be performed on a first system of a vendor who provides and/or maintains such an estimation model and/or a recommendation model and/or has access to training samples used to generate the estimation model and/or the recommendation model, while scan preparation based on the provided estimation model and/or recommendation model may be performed on a second system of a client of the vendor. In some embodiments, the generation of the estimation model and/or the recommendation model may be performed on a processing device, while the updating and application of the estimation model and/or the recommendation model may be performed on a different processing device. In some embodiments, the generation and/or updating of the estimation model and/or the recommendation model may be performed online in response to a request for scan preparation. In some embodiments, the generation and/or updating of the estimation model and/or the recommendation model may be performed offline.

In some embodiments, the estimation model and/or the recommendation model may be generated and/or updated (or maintained) by, e.g., the manufacturer of the medical device 110 or a vendor. For instance, the manufacturer or the vendor may load the estimation model and/or the recommendation model into the imaging system 100 or a portion thereof (e.g., the processing device 120) before or during the installation of the medical device 110 and/or the processing device 120, and maintain or update the estimation model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 150. The program may include a new model (e.g., a new estimation model and/or a new recommendation model) or a portion of a model that substitute or supplement a corresponding portion of the model.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the medical device 110, the terminal(s) 140, and/or the storage device 130 via the network 150. As another example, the processing device 120 may be directly connected to the medical device 110, the terminal(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal(s) 140 and/or the processing device 120. For example, the storage device 130 may store a first parameter set to a physiological motion of a subject to be scanned acquired before a scan is performed on the subject. As another example, the storage device 130 may store an estimation model and/or the recommendation model for scan preparation, etc. In some embodiments, the storage device 130 may store data and/or instructions that the processing device 120 may execute or use to perform exemplary methods/systems described in the present disclosure. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal(s) 140, etc.). One or more components in the imaging system 100 may access the data or instructions stored in the storage device 130 via the network 150. In some embodiments, the storage device 130 may be directly connected to or communicate with one or more other components in the imaging system 100 (e.g., the processing device 120, the terminal(s) 140, etc.). In some embodiments, the storage device 130 may be part of the processing device 120.

In some embodiments, a user (e.g., a doctor, a technician, or an operator) may interact with the imaging system 100 through the terminal (s) 140. For example, scan parameters determined during scan preparation may be displayed on an interface of the terminal 140. The user may perform one or more user operations with respect to the scan parameters via the terminal 140. As another example, an image generated by a scan performed according to the scan parameters may be displayed on an interface of the terminal 140. The user may perform a user operation to adjust the scan parameters via the terminal 140 until the image satisfies an image quality. In some embodiments, the terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the processing device 120.

The network 150 may include any suitable network that can facilitate the exchange of information and/or data for the imaging system 100. In some embodiments, one or more components of the medical device 110 (e.g., a CT device, a PET device, etc.), the terminal(s) 140, the processing device 120, the storage device 130, etc., may communicate information and/or data with one or more other components of the imaging system 100 via the network 150. For example, the processing device 120 may obtain parameter sets relating to the physiological motion of the subject acquired before a scan is performed on the subject from the detection device or the storage device 130 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

In some embodiments, the imaging system 100 may further include a detection device (not shown) configured to acquire/detect a physiological motion of the subject. For example, the detection device may acquire the physiological motion of the subject before an actual scan is performed on the subject (e.g., when the subject is not undergoing any scan or when the subject is undergoing a simulated scan). As another example, the detection device may acquire the physiological motion of the subject when an actual scan is being performed on the subject. In some embodiments, the detection device may include a detection device (e.g., an electrocardiogramonitor), or a mobile device (e.g., a smart device, a wearable device, etc.), a tablet computer, a laptop computer, etc., which may be installed with an application to record the physiological motion of the subject. In some embodiments, the detection device may be connected to the network 150 to communicate with one or more components of the imaging system 100. One or more components of the imaging system 100 may access data/information from the detection device via the network 150. In some embodiments, the detection device may be directly connected to or communicate with one or more components of the imaging system 100 (e.g., the processing device 120, the terminal(s) 140, etc.). In some embodiments, the detection device may be independent of the imaging system 100 but able to communicate with the imaging system 100 (e.g., via the network 150).

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the imaging system 100 may include one or more additional components and/or one or more components of the imaging system 100 described above may be omitted. Additionally or alternatively, two or more components of the imaging system 100 may be integrated into a single component. A component of the imaging system 100 may be implemented on two or more sub-components.

FIG. 2 is a schematic diagram illustrating hardware and/or software components of an exemplary computing device 200 may be implemented according to some embodiments of the present disclosure. The computing device 200 may be used to implement any component of the imaging system as described herein. For example, the processing device 120 and/or a terminal 140 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load. As illustrated in FIG. 2, the computing device 200 may include a processor 210, storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical device 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the medical device 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
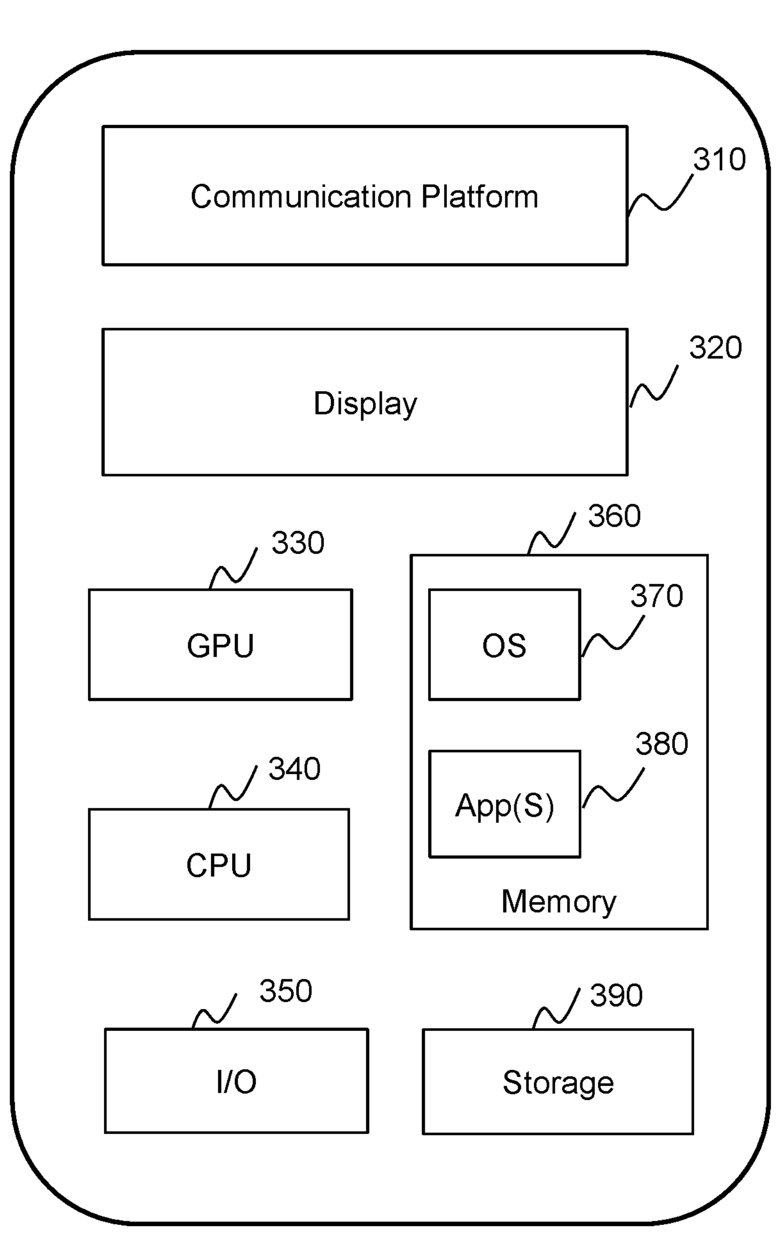
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. In some embodiments, one or more components (e.g., a terminal 140 and/or the processing device 120) of the imaging system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., IOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
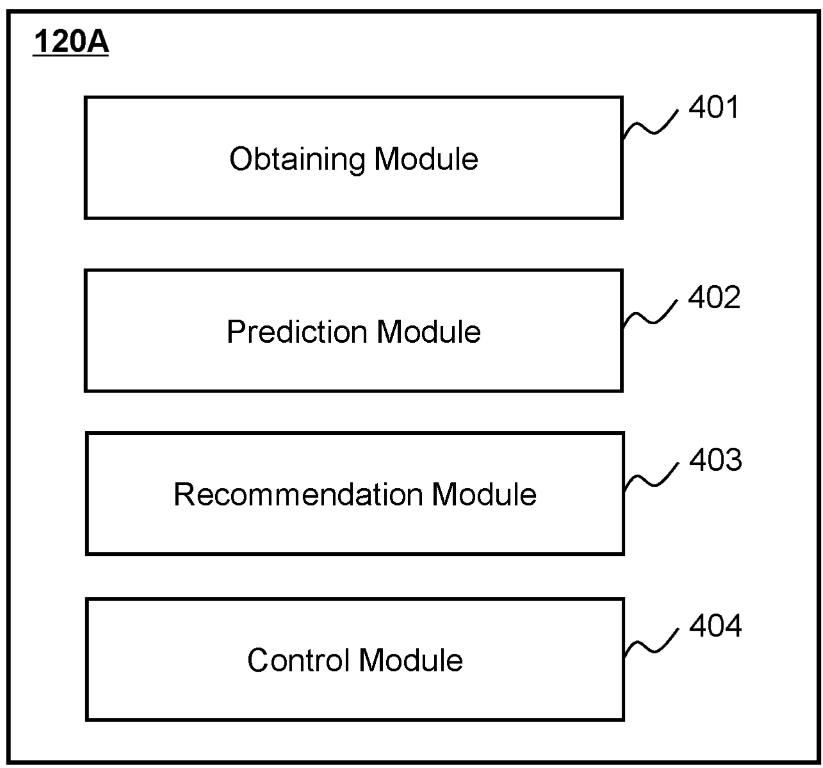
FIG. 4A and FIG. 4B are block diagrams illustrating exemplary processing devices according to some embodiments of the present disclosure.
Figure 4B:
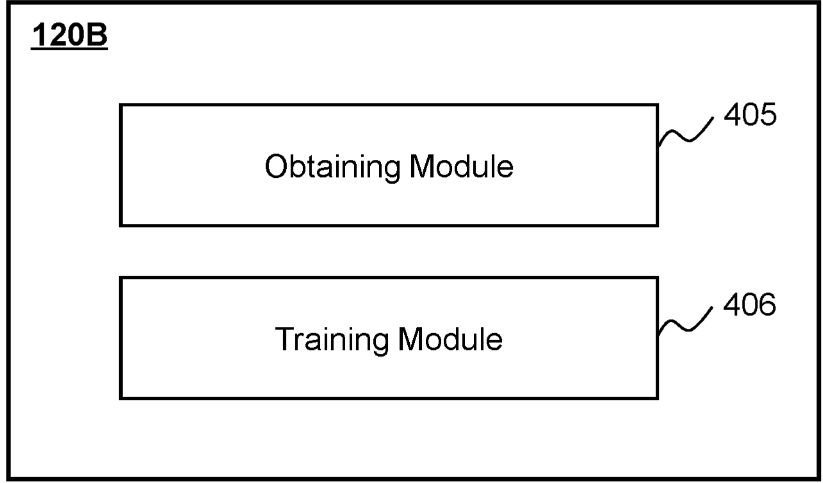

FIG. 4A and FIG. 4B are block diagrams illustrating exemplary processing devices 120A and 120B according to some embodiments of the present disclosure. In some embodiments, the processing devices 120A and 120B may be embodiments of the processing device 120 as described in connection with FIG. 1. In some embodiments, the processing devices 120A and 120B may be respectively implemented on a processing unit (e.g., the processor 210 illustrated in FIG. 2 or the CPU 340 as illustrated in FIG. 3). Merely by way of example, the processing devices 120A may be implemented on a CPU 340 of a terminal device, and the processing device 120B may be implemented on a computing device 200. Alternatively, the processing devices 120A and 120B may be implemented on a same computing device 200 or a same CPU 340. For example, the processing devices 120A and 120B may be implemented on a same computing device 200.

As shown in FIG. 4A, the processing device 120A may include an obtaining module 401, a prediction model 402, a recommendation model 403, and a control module 404.

The obtaining module 401 may be configured to obtain data/information from one or more components of the imaging system 100. For example, the obtaining module 401 may obtain a first parameter set of a subject to be scanned by a medical device (e.g., the medical device 110). The first parameter set of the subject may be acquired before the medical device performs a scan on the subject. In some embodiments, the first parameter set may be acquired by a detection device (e.g., an ECG monitor). As another example, the obtaining module 401 may obtain an estimation model and/or a recommendation model from the storage device 130, the terminal(s) 140 or an external source. As still another example, the obtaining module 401 may obtain health information of the subject. As a further example, the obtaining module 401 may obtain a characteristic of an operator of the scan, a demand relating to image quality of the scan, an imaging type of the scan, product information of the medical device, a type of the medical device, a characteristic of a prior image of the subject, one or more preliminary scans of the subject, or the like, or any combination thereof. As further another example, the obtaining module 401 may obtain a user input from the terminal(s) 140 of the imaging system. More descriptions regarding the obtained data (e.g., the first parameter set of the subject, models, health information of the subject, the user input, etc.) may be found elsewhere in the present disclosure.

The prediction module 402 may be configured to predict a second parameter set of the subject on an assumption that the scan is performed on the subject. In some embodiments, the prediction module 402 may predict the second parameter set of the subject by inputting the first parameter set into the estimation model. In some embodiments, the prediction module 402 may predict the second parameter set of the subject by inputting the first parameter set and the health information of the subject into the estimation model. More descriptions regarding the second parameter set and the prediction of the second parameter set may be found elsewhere in the present disclosure (e.g., operation 503 and the description thereof).

The recommendation module 403 may be configured to determine at least one scan parameter for the scan. In some embodiments, the recommendation module 403 may determine the at least one scan parameter for the scan based at least in part on the second parameter set of the subject using the recommendation model. For example, the recommendation module 403 may determine the at least one scan parameter for the scan by inputting the second parameter set of the subject and/or the health information of the subject into the recommendation model. More descriptions regarding the at least one scan parameter and the determination of the at least one scan parameter may be found elsewhere in the present disclosure (e.g., operation 505 and the descriptions thereof).

The control module 404 may be configured to control operations of modules or components of the imaging system 100. For example, the control module 404 may cause the at least one scan parameter to be presented to a user. As another example, the control module 404 may cause the medical device to perform the scan on the subject based on the at least one scan parameter. As still another example, the control module 404 may cause an image generated based on the scan to be presented to the user. More descriptions regarding causing the medical device to perform the scan on the subject based on the at least one scan parameter may be found elsewhere in the present disclosure (e.g., operation 507 and the description thereof).

As shown in FIG. 4B, the processing device 120B may include an obtaining module 405 and a training module 406.

The obtaining module 405 may be configured to obtain data/information used for model training. For example, the obtaining module 405 may obtain a plurality of first training samples used for generating an estimation model. As another example, the obtaining model 405 may obtain a plurality of second training samples used for generating a recommendation model. As still another example, the obtaining module 405 may obtain a first machine learning model used for generating the estimation model. As a further example, the obtaining module 405 may obtain a second machine learning model used for generating the recommendation model. More descriptions regarding the training samples and/or the machine learning models may be found elsewhere in the present disclosure (e.g., FIGS. 6-9 and the descriptions thereof).

The training module 406 may be configured to generate a trained model (e.g., the estimation model and/or the recommendation model). For example, the training module 406 may generate the estimation model by training the first machine learning model using the plurality of first training samples. As another example, the training module 4-6 may generate the recommendation model by training the second machine learning model using the plurality of second training samples. More descriptions regarding the training process(es) may be found elsewhere in the present disclosure (e.g., operation 603, operation 803, and the descriptions thereof).

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. Each of the modules described above may be a hardware circuit that is designed to perform certain actions, e.g., according to a set of instructions stored in one or more storage media, and/or any combination of the hardware circuit and the one or more storage media.

In some embodiments, the processing device 120A and/or the processing device 120B may share two or more of the modules, and any one of the modules may be divided into two or more units. For instance, the processing devices 120A and 120B may share a same obtaining module, that is, the obtaining module 401 and the obtaining module 405 are a same module. In some embodiments, the processing device 120A and/or the processing device 120B may include one or more additional modules, such as a storage module (not shown) for storing data. In some embodiments, the processing device 120A and the processing device 120B may be integrated into one processing device 120. In some embodiments, the generation of the estimation model and the generation of the recommendation model may be achieved by two different processing devices 120B respectively.

Figure 5:
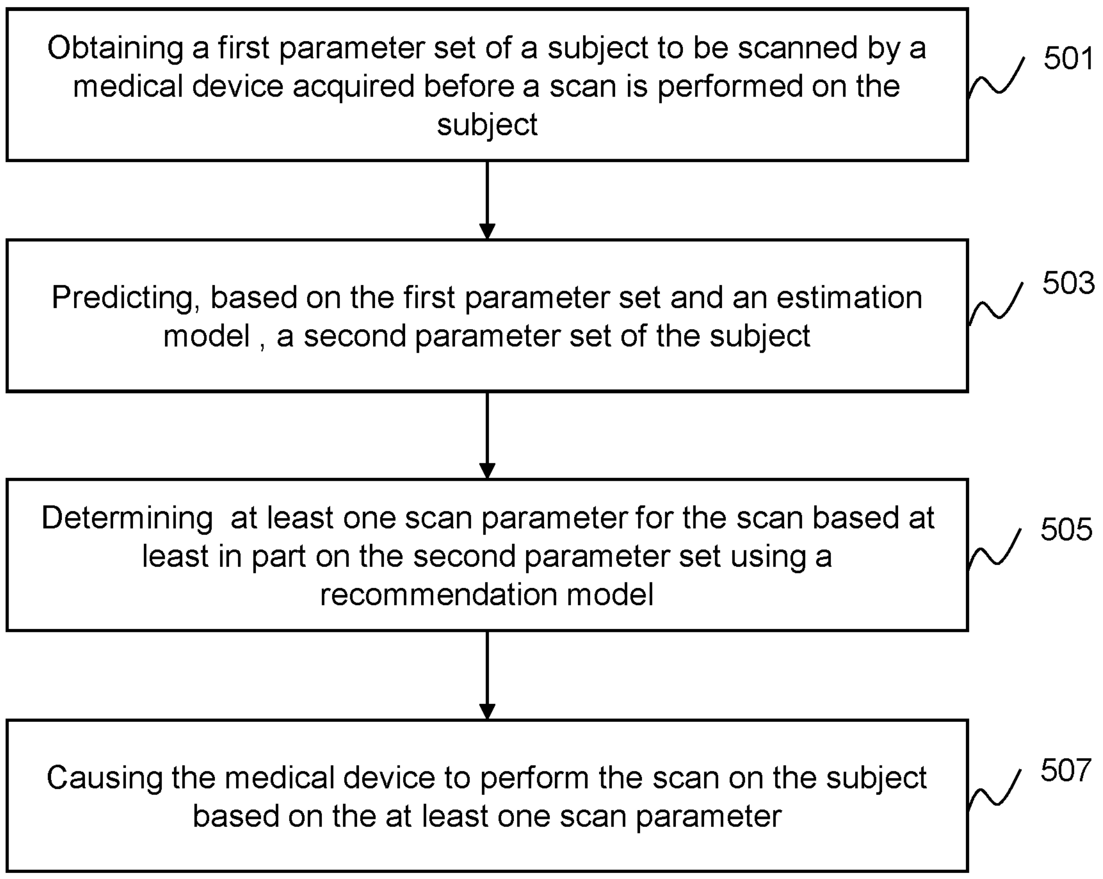
FIG. 5 is a flowchart illustrating an exemplary process for scan preparation according to some embodiments of the present disclosure.

FIG. 5 is a flowchart illustrating an exemplary process for scan preparation according to some embodiments of the present disclosure. In some embodiments, process 500 may be implemented as a set of instructions (e.g., an application) stored in a storage device (e.g., the storage device 130, the storage 220, and/or the storage 390). The processing device 120A (e.g., the processor 210, the CPU 340, and/or one or more modules illustrated in FIG. 4A) may execute the set of instructions, and when executing the instructions, the processing device 120A may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In some embodiments, before a medical device (e.g., the medical device 110) performs a scan on a subject (e.g., a patient), scan parameters for the scan may need to be determined. Traditionally, the scan parameters may be determined by a user according to experience or be recommended automatically according to the performance of the medical device, which may be inaccurate and unable to account for differences among different subjects. The scan parameters may need to be adjusted during the scan, which is time-consuming. Due to the lack of a more accurate and/or objective guidance in the scan planning, a user (e.g., a doctor) tends to increase a radiation dose of the scan to improve the chances of a successful scan, thereby causing an increased amount of radiation received by the subject during the scan. In some embodiments, the process 500 may be performed for determining the scan parameters more efficiently and accurately. For illustration purposes, the process 500 is described with reference to a scan associated with a cardiac angiography (also referred to as a cardiac angiography scan). During the cardiac angiography scan, the subject may need to be injected with a contrast agent and then hold his/her breath for a time period. The injection of the contrast agent may affect a heart rate of the subject which in turn has an impact on the cardiac angiography scan. It should be noted that the process 500 is appliable to any other scan during which the subject needs to hold his/her breath for a time period.

In 501, the processing device 120A (e.g., the obtaining module 401) may obtain a first parameter set of a subject (e.g., a patient) to be scanned by a medical device (e.g., the medical device 110) acquired before a scan is performed on the subject.

The first parameter set of the subject may relate to a physiological motion of the subject acquired before the scan is performed on the subject. The physiological motion of the subject may relate to cardiac motion, respiratory motion, etc., of the subject. Taking the cardiac angiography scan as an example, the first parameter set of the subject may include e.g., one or more parameters relating to a heart rate of the subject before the scan is performed on the subject. The one or more parameters may include an average heart rate, a heart rate fluctuation, etc., of the subject. For instance, the average heart rate of the subject may be, e.g., 60 beats/min, 70 beats/min, or 80 beats/min during a certain time period (e.g., for 5 minutes) before the scan is performed on the subject. As used herein, the heart rate fluctuation refers to a change of the heart rates of the subject, or a fluctuation range of the change of the heart rates of the subject, during a certain time period. For example, the heart rate fluctuation 10 minutes before a scan may be assessed in terms of a fluctuation range of the heart rates within the period (10 minutes before the scan), e.g., 60-90 beats/min, 70-90 beats/min, 80-105 beats/min, etc. As another example, the heart rate fluctuation before a scan may be assessed in terms of a change of the heart rate, or an average heart rate of the subject over time, e.g., 60 beats/min in a first 2 minutes, an average heart rate of 65 beats/min in a second 2 minutes, etc.

In some embodiments, the first parameter set of the subject may include a first parameter sub-set acquired during a first time period (e.g., 5 minutes, 10 minutes, etc.), a second parameter sub-set acquired during a second time period different from the first time period, or the like, or any combination thereof. The second time period may be substantially the same as the scan time of the scan. The subject may be not undergoing any scan during the first time period. For example, the subject may be in a calm and free-breathing state during the first time period. The calm and free-breathing state refers to a state in which the subject remains calm physically and emotionally and breathes freely. The subject may be undergoing a simulated scan during the second time period. Taking the cardiac angiography scan as an example, the simulated scan may be performed by simulating a portion of, but not all, the conditions of the cardiac angiography scan. For instance, the simulated scan may be performed by setting up the subject on the table of the medical device, causing the table of the medical device to move and/or be positioned as in an actual scan, allowing the simulated scan to last for a scan time, generating a sound that mimics the sound generated during an actual scan when the subject is not actually injected with the contrast agent and no radiation is delivered to the subject for image scanning. The subject may be asked to hold his/her breath during the simulated scan if the subject is going to be asked to do so in an actual scan.

In some embodiments, the first parameter set of the subject may be acquired by one or more detection devices (e.g., a single detection device or two different detection devices) as described in FIG. 1. For example, an ECG monitor may acquire and record ECG signals of the subject during the first time period and the second time period. The processing device 120A may determine the first parameter set of the subject based on the ECG signals. As another example, the first parameter sub-set may be acquired by a wearable device (e.g., a sports bracelet, a sports watch, a heart rate monitor, an in-ear heart rate sensor, etc.) the subject wears and the second parameter sub-set may be acquired by the ECG monitor. The wearable device may detect heart rates of the subject in different states (e.g., when the subject gets up in the morning, when the subject is asleep, when the subject is eating, when the subject is walking, when the subject is on a bus, when the subject is talking, when the subject is working, when the subject is exercising, etc.) and label the detected heart rates with corresponding states. The processing device 120A may determine the first parameter sub-set based on historical heart rates of the subject recorded by a wearable device. The ECG monitor may acquire ECG signals of the subject when the simulated scan is performed on the subject. The processing device 120A may determine the second parameter sub-set based on the ECG signals. As a further example, the detection device may detect pulse signals of the subject during the first time period and the second time period. The processing device 120A may determine the first parameter set of the subject based on the pulse signals of the subject.

In 503, the processing device 120A (e.g., the prediction module 402) may predict, based at least in part on the first parameter set and an estimation model, a second parameter set of the subject.

In some embodiments, the processing device 120A may predict, based on the first parameter set and an estimation model, a second parameter set of the subject. In some embodiments, the processing device 120A may predict, based on the first parameter set, the health information of the subject, and an estimation model, a second parameter set of the subject. The health information of the subject may include an age of the subject, a gender of the subject, a body mass index (BMI) of the subject, a medication that the subject has been or is taking, information associated with a portion to be scanned of the subject, information relating to an injection of the contrast agent, information of a goal of diagnosis and treatment (e.g., an assessment of coronary stenosis, an analysis of cardiac function, etc.), a history of any medical condition of the subject (e.g., whether the subject has an arrhythmia or a type of the arrhythmia), a breath-holding capacity of the subject, a breath frequency of the subject, or the like, or any combination thereof. In some embodiments, the health information of the subject may further include textual medical information (e.g., past medical history, etc), image information and examination results of other modalities (e.g., ultrasound images, etc).

Similar to the first parameter set of the subject, the second parameter set of the subject may relate to the physiological motion of the subject (e.g., on an assumption that the scan is performed on the subject) (also referred to as a predicted physiological motion). The predicted physiological motion of the subject may relate to a predicted heart rate, a predicted pressure, a predicted breathing, a predicted temperature, etc. of the subject. Taking the cardiac angiography scan as an example, the second parameter set of the subject may relate to a predicted cardiac motion of the subject. The second parameter set of the subject may include one or more parameters relating to, e.g., a predicted heart rate of the subject. For instance, the second parameter set of the subject may include a predicted average heart rate, a predicted heart rate fluctuation, etc., of the subject. The second parameter set of the subject may include one or more parameters similar to those of the first parameter set of the subject except that the timing and/or conditions that the parameter(s) describe(s) are different. For instance, both the first parameter set and the second parameter set include parameters relating to the heart rate of the subject; the first parameter set includes parameters relating to the heart rate of the subject before a scan, while the second parameter set includes parameters relating to the heart rate of the subject during a simulated or actual scan.

As used herein, an estimation model refers to a model configured to determine a second parameter set of the subject based at least in part on the first parameter set of the subject. For the cardiac angiography scan, the estimation model may also be referred to as a heart rate prediction model. The estimation model may be a machine learning model or a statistical model. For instance, the estimation model may be a classification and logistic regression (Logistic Regression) model, a k-nearest neighbor (kNN) model, a Naive Bayes (NB) model, a support vector machine (SVM) model, a decision tree (DT) model, a random forest (RF) model, a classification and regression trees(CART) model, a gradient boosting decision tree (GBDT) model, an extreme gradient boosting (XGBoost) model, a light gradient boosting machine (LightGBM) model, a gradient boosting machine (GBM) model, a least absolute shrinkage and selection operator (LASSO) model, an artificial neural networks (ANN) model, or the like, or any combination thereof.

In some embodiments, the estimation model may be a trained machine learning model, e.g., a trained sequence model. As used herein, the trained sequence model refers to a connectionist model configured to sequentially process an input dataset including a plurality of data points associated with each other in time. The trained sequence model may include a trained recurrent neural network (RNN) (e.g., a trained Long Short-Term Memory (LSTM) model), a trained autoregressive (AR) model, a trained moving average (MA) model, a trained autoregressive moving average (ARMA) model, a trained autoregressive integrated moving average (ARIMA) model, a trained vector autoregression (VAR) model, a trained structural VAR (SVAR) model, or the like, or any combination thereof.

Taking the trained LSTM model as an example, the estimation model may include a plurality of sequentially connected trained neural networks each of which includes an input layer, a hidden layer, and an output layer. As used herein, a layer may refer to an algorithm or a function for processing an input of the layer. The sequentially connected trained neural networks may include a first trained neural network and at least one second trained neural network downstream to the trained first neural network. A hidden layer of a second trained neural network may be connected with a hidden layer of an upstream trained neural network and a hidden layer of a downstream trained neural network. The hidden layer of a trained neural network may include a cell configured to "remember" values over arbitrary time intervals. The cell may include an input gate, an output gate, and a forget gate. The input gate may be configured to control the input of new information that flows into the cell. The forget gate may be configured to determine the information that remains in the cell. The output gate may be configured to determine the information that is outputted from the cell. Such a structure of the estimation model may pass the influence of an upstream trained neural network onto a downstream trained neural network connected with the upstream trained neural network. That is, an output of the upstream trained neural network may be input to the downstream trained neural network, thereby affecting an output of the downstream trained neural network.

During the application of the estimation model, an input of the estimation model may include the first parameter set (e.g., including a plurality of heart rates over a sequence of different time points), an input of the first trained neural network of the estimation model may include one of the plurality of heart rates at a first time point of the different time points in the sequence, and an input of each second trained neural network of the estimation model may include one of the plurality of heart rates at a corresponding time point in the sequence and an output of an upstream trained neural network connected with the second trained neural network. In some embodiments, an input of the estimation model may further include the health information of the subject, and an input of the first trained neural network of the estimation model may also include the health information of the subject. In some embodiments, the processing device 120A may directly input the first parameter set of the subject into the estimation model, and the estimation model may output the second parameter set of the subject. In some embodiments, the processing device 120A may directly input the first parameter set of the subject and the health information of the subject into the estimation model, and the estimation model may output the second parameter set of the subject. Alternatively, the processing device 120A may preprocess the health information of the subject, e.g., by performing a word segmentation operation on the health information. The processing device 120A may input the preprocessed health information and the first parameter set into the estimation model, and the estimation model may output the second parameter set of the subject.

In some embodiments, the processing device 120A (e.g., the obtaining module 401) may obtain the estimation model from one or more components of the imaging system 100 (e.g., the storage device 130, the terminals(s) 140) or an external source via a network (e.g., the network 150). For example, the estimation model may be previously trained by a computing device (e.g., the processing device 120B), and stored in a storage device (e.g., the storage device 130, the storage 220, and/or the storage 390) of the imaging system 100. The processing device 120A may access the storage device and retrieve the estimation model. In some embodiments, the estimation model may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the estimation model may be a supervised learning algorithm, a semi-supervised learning algorithm, an unsupervised learning algorithm, or the like. In some embodiments, the estimation model may be generated by a computing device (e.g., the processing device 120B) by performing a process (e.g., process 600) for generating an estimation model disclosed herein. More descriptions regarding the generation of the estimation model may be found elsewhere in the present disclosure. See, e.g., FIGS. 6-7 and relevant descriptions thereof.

In some embodiments, the estimation model may be an inverse Gaussian probability model. The inverse Gaussian probability model may be derived from a physiological mechanism of generating ECG signals. The generation of the ECG signals comes from an autonomic electrical activity of a sinoatrial node of a heart and is innervated. Although an input of sympathetic and parasympathetic nerves to the sinoatrial node lasts for a short time, its influence may last for a few seconds, that is, a current heart rate may relate to a historical heart rate (e.g., the first parameter set). In such cases, the current heart rate may be expressed as a linear combination of historical heart rate signals with time-varying parameters and variances. Taking the inverse Gaussian probability model as the estimation model, a heart rate prediction (e.g., a prediction of the second parameter set) may be achieved by determining the time-varying parameters of the inverse Gaussian probability model using a point process adaptive prediction algorithm in combination with a correlation of the heart rate signals.

In some embodiments, the estimation model may be configured to predict the heart rate (e.g., the second parameter set) based on a physiological function of the subject. As an activity level of the subject correlates with a physiological energy demand experienced by the subject, the activity level may be transformed into an inferred value of a physiological load. When the physiological load is applied to the physiological function of the subject, the subject may match an amount of oxygen delivered to muscles with the physiological load by changing the heart rate and heart stroke volume. In such cases, for a certain sustainable physiological load, the subject may have a specific heart rate at which the supply of oxygen matches the demand for metabolic energy. In the estimation model, a target heart rate may refer to a heart rate (e.g., the second parameter set) in a specific activity state under a constant physiological load. The specific activity state may be a calm and free-breathing state and/or a simulated scan state of the subject.

In some embodiments, the estimation model may predict a heart rate according to a relationship between the heart rate and the energy consumption of the subject. For example, the processing device 120A may obtain an acceleration vector using an accelerometer during an activity of the subject and determine a resultant acceleration that is generated by the subject during the activity. The processing device 120A may establish a relationship model between the resultant acceleration and the energy consumption by analyzing a change of the resultant acceleration over time and determining a change of the energy consumption of the subject during the activity process. The processing device 120A may obtain basic information of the subject and determine a baseline metabolic rate, a maximum heart rate, an oxygen uptake at the maximum heart rate, and an energy consumption at the maximum heart rate, etc., of the subject to establish a relationship model between the heart rate and the energy consumption of the subject during the activity. The energy consumption may include an energy consumption X during the activity that is determined according to a change of the acceleration and an energy consumption $X_{max}$ at the maximum heart rate. The processing device 120A may determine the change of heart rate according to the change of energy consumption to predict the heart rate of the subject during the activity. The activity may include that the subject is in a calm and free-breathing state and/or in a simulated scanning state.

In some embodiments, the estimation model may be an adaptive model. The adaptive model may include at least one adaptive parameter. The processing device 120A may obtain information regarding the physical exertion of the subject. In some embodiments, the information regarding physical exertion of the subject may be determined based on movement data of the subject during a time period. The movement data of the subject may be acquired by a wearable device that the subject wears. The processing device 120A may determine a predicted power output of the subject based at least in part on the information regarding physical exertion of the subject and a portion of the adaptive model. The processing device 120A may determine a demand value of the heart rate of the subject based at least in part on the predicted power output of the subject and the at least one adaptive parameter using the adaptive model. The demand value of the heart rate may indicate the heart rate suitable for sustaining an activity currently performed by the subject with aerobic respiration. The processing device 120A may also obtain heart rate information of the subject (e.g., the first parameter set of the subject as described in operation 510). The heart rate information of the subject may be acquired at the same time period as the information regarding the physical exertion of the subject. The processing device 120A may determine a predicted heart rate (e.g., the second parameter set) of the subject based on the demand value of the heart rate and the heart rate information. In some embodiments, the at least one adaptive parameter may be adjustable, which can be provided as feedback to the adaptive model over time. For example, the at least one adaptive parameter may be adjusted by comparing the demand value of the heart rate and the predicted value of the heart rate using adaptive learning. As another example, the processing device 120A may determine an improved predicted value of the heart rate based on the demand value of the heart rate and the predicted value of the heart rate. The at least one adaptive parameter may be adjusted by comparing the demand value of the heart rate and the improved predicted value of the heart rate using adaptive learning.

In 505, the processing device 120A (e.g., the recommendation module 403) may determine at least one scan parameter for the scan based at least in part on the second parameter set using a recommendation model.

In some embodiments, the at least one scan parameter may include the number (or count) of cardiac cycles during the scan, a first phase range during the scan, a pitch of the medical device, a second phase range relating to a radiation dose control, exposure time, a dose range relating to the radiation dose control, a voltage of a tube of the radiation source, an electricity of the tube of the radiation source, a signal-to-noise ratio (SNR) of the medical device, or the like, or any combination thereof. The count of cardiac cycles during the scan refers to a certain count of cardiac cycles (e.g., 3 cardiac cycles) within which the scan may be performed on the subject.

The first phase range during the scan refers to a certain phase range within a cardiac cycle during which scan data (e.g., image data) is acquired when the scan is performed on the subject. For instance, the first phase range during the scan may be 30%~70% of a cardiac cycle. Specifically, one cardiac cycle may be designated as a motion phase. The duration of one cardiac cycle may be set as 1. Scan data within the phase range of 30%~70% (i.e., a time range of 0.3~0.7 of the entire cardiac cycle) may be acquired, and scan data within the remaining phase range may not be acquired, which can further shorten the exposure time of the radiation source and reduce the impact of the scan on the subject. The pitch of the medical device may also be referred to as a spiral pitch or a helical pitch of the medical device. The pitch of the medical device is defined as a ratio (e.g., 0.5, 3.5, 5.5, etc.) of a table distance traveled within one helical turn over to the longitudinal beam aperture of a detector (e.g., an x-ray detector) of the medical device used in the scan. The second phase range relating to the radiation dose control refers to a certain phase range during which the dose of the imaging radiation may be adjusted. For instance, a high-dose scan may be performed in a phase range of 0.45~0.85 of a cardiac cycle, and a low-dose scan may be performed in the remaining phase ranges of the cardiac cycle. A first dose of the imaging radiation may be used during the high-dose scan. A second dose of the imaging radiation may be used during the low-dose scan. The value of the first dose may be greater than a preset dose value. The value of the second dose may be less than a preset dose value. Alternatively, the value of the second dose is less than a certain percentage (e.g., 50%, 40%, etc.) of the value of the first dose. The exposure time refers to a duration (e.g., a length of time) when the subject is radiated by the radiation source of the medical device. For instance, the exposure time may be 1 second, 2 seconds, etc. The dose range relating to the radiation dose control refers to a range of demand dose (e.g., 1 millisievert (mSv)~3 mSvs) of the radiation for the scan to be performed on the subject. The voltage of the tube of the radiation source refers to a voltage (e.g., 120 kv) of the tube when the scan is performed on the subject. The current of the tube of the radiation source refers to an electricity (e.g., 50 mA) of the tube when the scan is performed on the subject. The SNR of the medical device refers to a ratio of a signal of the medical device to the noise of the medical device, for example, 80 dB.

In some embodiments, the processing device 120A may set at least one default scan parameter for the scan before obtaining the first parameter set of the subject. The processing device 120A may adjust the at least one default scan parameter according to the at least one scan parameter determined using the recommendation model.

In some embodiments, the processing device 120A may obtain a recommendation model. In some embodiments, the processing device 120A may determine the at least one scan parameter for the scan by inputting the second parameter set of the subject into the recommendation model. In some embodiments, the processing device 120A may obtain health information of the subject. In some embodiments, the processing device 120A may determine the at least one scan parameter for the scan by further inputting the health information, in addition to the second parameter set, of the subject into the recommendation model. The health information of the subject may include an age of the subject, a gender of the subject, a body mass index (BMI) of the subject, a medication that the subject has been or is taking, information associated with a portion to be scanned of the subject, information relating to an injection of the contrast agent, information of a goal of diagnosis and treatment (e.g., an assessment of coronary stenosis, an analysis of cardiac function, etc.), a history of any medical condition of the subject (e.g., whether the subject has an arrhythmia or a type of the arrhythmia), a breath-holding capacity of the subject, a breath frequency of the subject, or the like, or any combination thereof. In some embodiments, the processing device 120A may directly input the second parameter set of the subject and the health information of the subject into the recommendation model, and the recommendation model may output the at least one scan parameter for the scan. Alternatively, the processing device 120A may preprocess the health information of the subject, e.g., by performing a word segmentation operation on the health information. The processing device 120A may input the preprocessed health information and the second parameter set into the recommendation model, and the recommendation model may output the at least one scan parameter for the scan. More descriptions regarding the preprocess operation may be found elsewhere in the present disclosure (e.g., FIG. 8 and the description thereof).

In some embodiments, the processing device 120A may also obtain a characteristic of an operator of the scan, a demand relating to image quality of the scan, an image type of the scan, product information of the medical device, a type of the medical device, a characteristic of a prior image of the subject, one or more preliminary scans of the subject, or the like, or any combination thereof. As used herein, the characteristic of the operator refers to a personal characteristic of the operator, including a gender, a height, medical experience, etc., of the operator. The demand relating to image quality refers to the desired image quality of a resultant image of the scan, which can be divided into a high image quality, an intermediate image quality, a low image quality, etc. The image type refers to a format of an image generated by the scan, including bitmap (bmp), joint photographic expert group (jpg or jpeg), portable network graphic (png), tagged image file format (tif or tiff), graphic interchange format (gif), PC paintbrush exchange (pcx), tagged graphic (tga), etc. The product information of the medical device may include a manufacturer, a device model, operation specifications, a weight, a price, a power, etc. The type of the medical device may include a CT device, an X-ray imaging device, a DR device, a SPECT device, a PET-CT device, an X-ray-MRI device, a SPECT-MRI device, a CT guided radiotherapy device, etc. The characteristic of a prior image of the subject may relate to a prior scan performed on the subject. The characteristic of a prior image may include, e.g., an image quality of the prior image. The one or more preliminary scans of the subject may refer to scan(s) performed on the subject during the scan preparation for, e.g., positioning the subject. In some embodiments, the recommendation model may be applicable for different types of medical devices by taking the type of the medical device as an input of the recommendation model. In such occasions, the recommendation model may be trained using training samples associated with different types of medical devices. In some embodiments, the recommendation model may be applicable for a specific type of the medical device when the recommendation model is generated using training samples associated with the specific type of the medical device.

As used herein, a recommendation model may be configured to determine at least one scan parameter for a scan according to at least in part the second parameter set of the subject. The recommendation model may also be referred to as a scan parameter recommendation model. The recommendation model may be a statistical model or a machine learning model. For instance, the recommendation model may include an LR model, a kNN model, an NB model, an SVM model, a DT model, an RF model, a CART model, a GBDT model, an XGBoost model, a LightGBM model, a GBM model, a LASSO model, an ANN model (e.g., a neural network model), a self-teaching model, or the like, or any combination thereof. In some embodiments, a model structure of the recommendation model may be the same as or different from that of the estimation model. For example, the recommendation model may be a statistical model, and the estimation model may be a machine learning model. As another example, the recommendation model may be a convolutional neural network (CNN) model, and the estimation model may be an RNN model. As still another example, the recommendation model and the estimation model may be same neural network models.

In some embodiments, the recommendation model may be a second trained machine learning model, e.g., a trained CNN model. The trained CNN model may be configured to determine the at least one scan parameter as a classification problem. In some embodiments, the recommendation model may include at least one trained CNN model each of which corresponds to one of the at least one scan parameter.

For example, the scan parameter of the count of cardiac cycles during the scan may correspond to a first trained CNN model. The first trained CNN model may be configured to determine the count of cardiac cycles during the scan as a classification problem. An input of the first trained CNN model may include at least a portion of the second parameter set of the subject with or without the health information of the subject, and an output of the first trained CNN model may include the count of cardiac cycles during the scan (e.g., a positive integer within the range of 1 through 5).

As another example, the scan parameter of the first phase range during the scan may correspond to a second trained CNN model. The second trained CNN model may be configured to determine the first phase range during the scan as a classification problem. An input of the second trained CNN model may include at least a portion of the second parameter set of the subject with or without the health information of the subject, and an output of the second trained CNN model may include the first phase range during the scan (e.g., an interval within the range of 0 through 1).

In some embodiments, the recommendation model may be a combined model by combining the at least one trained CNN model (e.g., the first trained CNN model and the second trained CNN model). An input of the recommendation model may include at least a portion of the second parameter set of the subject with or without the health information of the subject, and an output of the recommendation model may include the at least one scan parameter.

In some embodiments, the processing device 120A (e.g., the obtaining module 401) may obtain the recommendation model from one or more components of the imaging system 100 (e.g., the storage device 130, the terminals(s) 140) or an external source via a network (e.g., the network 150). For example, the recommendation model may be previously trained by a computing device (e.g., the processing device 120B), and stored in a storage device (e.g., the storage device 130, the storage 220, and/or the storage 390) of the imaging system. In some embodiments, the recommendation model may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the recommendation model may be a supervised learning algorithm, a semi-supervised learning algorithm, an unsupervised learning algorithm, or the like. In some embodiments, the recommendation model may be generated by a computing device (e.g., the processing device 120B) by performing a process (e.g., process 800) for generating a recommendation model disclosed herein. More descriptions regarding the generation of the recommendation model may be found elsewhere in the present disclosure. See, e.g., FIGS. 8-9 and relevant descriptions thereof.

In some embodiments, the recommendation model may recommend the at least one scan parameter for the scan based further on a desired quality score of a resultant scan image. For instance, during the training of the recommendation model, the training data may include various scan images obtained based on various sets of scan parameters for at least some sample subjects. Each of such various scan images of a sample subject may correspond to a certain image quality assessed in terms of a quality score. In some embodiments, the quality score of a scan image may be assigned by a user, e.g., a doctor who has reviewed the scan image. The recommendation model may be trained to include a correspondence relationship between a quality score of a resultant scan image and the corresponding scan parameter set. In such cases, the recommendation model may select, based on the corresponding relationship, scan parameter set corresponding to a desired quality score of a resultant scan image. The scan parameter set corresponding to a lowest estimated dose of radiation absorption, among various candidate scan parameter sets, may be designated as the scan parameter(s) for the scan to be performed on the subject.

In 507, the processing device 120A (e.g., the control module 404) may cause the medical device to perform the scan on the subject based on the at least one scan parameter.

In some embodiments, the processing device 120A may cause at least a portion of the at least one scan parameter to be presented to a user (e.g., the doctor or technician) via the terminal 140. The processing device 120A may receive a user input from the user via the terminal 140. The processing device 120A may cause the medical device to perform the scan on the subject based on the at least one scan parameter and the user input if available. For example, the user input may include a confirmation of the at least one scan parameter. The processing device 120A may cause the medical device to perform the scan on the subject based on the at least one scan parameter in response to receiving a confirmation from the user. As another example, the user input may include an instruction for adjusting at least one of the at least one scan parameter. The processing device 120A may adjust the at least one scan parameter based on the user input. The processing device 120A may cause the medical device to perform the scan on the subject based on the at least one scan parameter with the adjustment according to the user input. In some embodiments, the processing device 120A may cause the medical device to perform the scan on the subject according to the at least one scan parameter to obtain an image. The processing device 120A may determine whether the image satisfies a preset condition, e.g., whether an image quality of the image satisfies a preset image quality. In response to determining that the image does not satisfy the preset condition, the processing device 120A may adjust the at least one scan parameter until a satisfactory image is generated from a scan performed on the subject based on the adjusted at least one scan parameter. In some embodiments, the situation that the image is unsatisfactory and/or the image itself may be presented to the user. The user may provide a further input including, e.g., an instruction on how to adjust the at least one scan parameter, a confirmation or instruction that the image is indeed unsatisfactory or not, etc. In response to determining that the image satisfies the preset condition, the processing device 120A may stop adjusting the at least one scan parameter. In such situation, the processing device 120A may cause the image to be presented to the user. The processing device 120A may receive a further user input including, e.g., a confirmation or instruction that the image is indeed satisfactory or not, an instruction on how to further adjust the at least one scan parameter.

In some embodiments, the processing device 120A may label the adjusted at least one scan parameter. The recommendation model may be updated based at least in part on the labeled adjusted scan parameter(s), the health information of the subject, and/or the second parameter set of the subject. For example, the labeled adjusted scan parameter (s), the health information of the subject, and the second parameter set of the subject corresponding to the scan may be added as a new training sample. When the number (or count) of new training samples exceeds a first threshold, the updating of the recommendation model may be triggered such that the new training samples are used to optimize the recommendation model. Alternatively, the recommendation model may be updated in response to receiving a user input relating to optimizing the recommendation model.

In some embodiments, the processing device 120A may obtain a third parameter set of the subject acquired when the scan is being performed on the subject. The third parameter set of the subject is a true parameter set corresponding to the second parameter set of the subject which is a predicted parameter set. The processing device 120A may determine a difference between the third parameter set of the subject and the second parameter set of the subject. The processing device 120A may determine whether to update the estimation model based at least in part on the difference. For example, the processing device 120A may determine whether the difference exceeds a preset difference threshold. The preset difference threshold may include an absolute value such as 10, 15, or 20, etc., describing a difference value between the second parameter set of the subject and the third parameter set of the subject. Alternatively, the preset difference threshold may include a relative value expressed in terms of, e.g., a percentage such as 80%, 85%, 90%, or 110%, 120%, etc., describing a ratio of the third parameter set of the subject to the second parameter set of the subject. In response to determining that the difference is less than the preset difference, the processing device 120A may not label the third parameter set. In response to determining that the difference exceeds the preset difference, the processing device 120A may label the third parameter set to be used in updating the estimation model. The estimation model may be updated based at least in part on the labeled third parameter set of the subject and the first parameter set of the subject. For instance, the labeled third parameter set of the subject and the first parameter set of the subject corresponding to the scan may be added as a new training sample. When the number (or count) of new training samples exceeds a second threshold, the updating of the estimation model may be triggered such that the new training samples may be used to optimize the estimation model. Alternatively, the estimation model may be updated in response to receiving a user input relating to optimizing the estimation model.

According to some embodiments of the present disclosure, scan parameter(s) for the scan may be determined using the estimation model and the recommendation model in consideration of a plurality of features such as the first parameter set of the subject and the health information of the subject, which can improve the accuracy of the determined scan parameter(s), thereby reducing scan time and the radiation dose received by the subject during the scan. In addition, the determined scan parameter(s) may be presented to the user for confirmation or further adjustment to allow user intervention of the scan preparation.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 500 may be omitted and/or one or more additional operations may be added. For example, a storing operation may be added elsewhere in the process 500. In the storing operation, the processing device 120A may store information and/or data (e.g., the at least one scan parameter, the estimation model, the recommendation model, etc.) associated with the imaging system 100 in a storage device (e.g., the storage device 130) disclosed elsewhere in the present disclosure. As another example, operation 503 and operation 505 may be achieved by performing a single operation. For instance, the estimation model and the recommendation model may be two components of a single trained machine learning model. In some embodiments, the processing device 120A may check if an abnormal state of the subject exists before a scan is performed. For instance, the subject rushes to the scan or is otherwise nervous and has an abnormally high heart rate; the processing device 120A may identify that the heart rate of the subject is abnormally high, and sends a notification to the user, or automatically halt the scan preparation to allow time for a remedial measurement. In some embodiments, the storage device may store a plurality of estimation models, e.g., corresponding to different genders, different ages, different types of disease, different breath states, different environmental conditions, or the like, or any combination thereof. The processing device 120A may select an estimation model from the storage device as the estimation model described in operation 503. In some embodiments, the estimation model may be a trained neural network model. The processing device 120A may obtain other information of the subject and/or environment feature(s). Exemplary other information may include physiological information and/or individual information including a gender of the subject, an age of the subject, an emotional state of the subject, a fatigued state of the subject, a medication that the subject has been or is taking, a breath-holding capacity of the subject, etc. Exemplary environment features may include a temperature, a humidity, an air pressure, etc., where the scan is to be taken The processing device 120A may determine the second parameter set by inputting the first parameter set with the other information of the subject and/or the environment features into the trained neural network model. In some embodiments, only the first parameter sub-set or the second parameter sub-set may be obtained in operation 501, and the second parameter set may be generated based on the first parameter sub-set or the second parameter sub-set and the estimation model.

FIG. 6 is a flowchart illustrating an exemplary process for generating an estimation model according to some embodiments of the present disclosure. In some embodiments, process 600 may be implemented as a set of instructions (e.g., an application) stored in a storage device (e.g., the storage device 130, storage 220, and/or storage 390). The processing device 120B (e.g., the processor 210, the CPU 340, and/or one or more modules illustrated in FIG. 4B) may execute the set of instructions, and when executing the instructions, the processing device 120B may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting. In some embodiments, the estimation model described in connection with operation 503 in FIG. 5 may be obtained according to the process 600. In some embodiments, the process 600 may be performed by another device or system other than the imaging system 100, e.g., a device or system of a vendor of a manufacturer. For illustration purposes, the implementation of the process 600 by the processing device 120B is described as an example.

In 601, the processing device 120B (e.g., the obtaining module 405) may obtain a plurality of first training samples. Each of the plurality of first training samples may include a first sample parameter set relating to a physiological motion of a sample subject acquired before a sample scan is performed on the sample subject and a second sample parameter set relating to the physiological motion of the sample subject acquired when the sample scan is being performed on the sample subject. In some embodiments, each of the plurality of first training samples may also include sample health information of the sample subject.

As used herein, a sample subject refers to an object whose data is used for training the estimation model. The sample subjects may meet a certain preset condition and include subjects of different genders and different ages. In some embodiments, the sample subjects may include the subject to be scanned as described in connection with FIG. 5. For example, data from the subject to be scanned obtained in one or more prior scans may be used as the training data for training the estimation model; a first training sample may include a prior first parameter set of the subject acquired when a prior scan is performed on the subject and a prior second parameter set of the subject acquired when the prior scan is being performed on the subject. The sample subjects may include subjects other than the subject to be scanned.

A sample first parameter set refers to a first parameter set of the sample subject that is acquired before a sample scan is performed on the subject, which is similar to the first parameter set of the subject as described in connection with operation 501. Merely by way of example, the first sample parameter set of the sample subject may include a first sample parameter sub-set (denoted as Trainning_HRrest) acquired during a first sample time period and a second sample parameter sub-set (denoted as Trainning_HRtest) acquired during a second sample time period. The sample subject may be in a calm and free-breathing state during the first sample time period. The sample subject may be undergoing a simulated scan during the second sample time period. A sample second parameter set (denoted as Training HR scan) refers to a ground truth parameter set of the sample subject that is acquired when the sample scan is being performed on the subject, which is similar to the third parameter set of the subject as described in connection with operation 507. A sample scan refers to a scan performed on the sample subject, which is the same as or similar to the scan to be performed on the subject as described in connection with FIG. 5. For example, the sample scan may include a sample cardiac angiography scan. A sample image generated based on the sample scan may be suitable for diagnosis purposes. For example, the sample image may satisfy a preset image quality. The sample health information of the sample subject refers to health information of the sample subject, which is similar to the health information of the subject as described in connection with operation 501.

In some embodiments, a first training sample may be previously generated and stored in a storage device (e.g., the storage device 130, the storage 220, the storage 390, or an external source). The processing device 120B may retrieve the first training sample directly from the storage device.

In 603, the processing device 120B (e.g., the training module 406) may generate the estimation model by training a first machine learning model using the plurality of first training samples.

Figure 7:
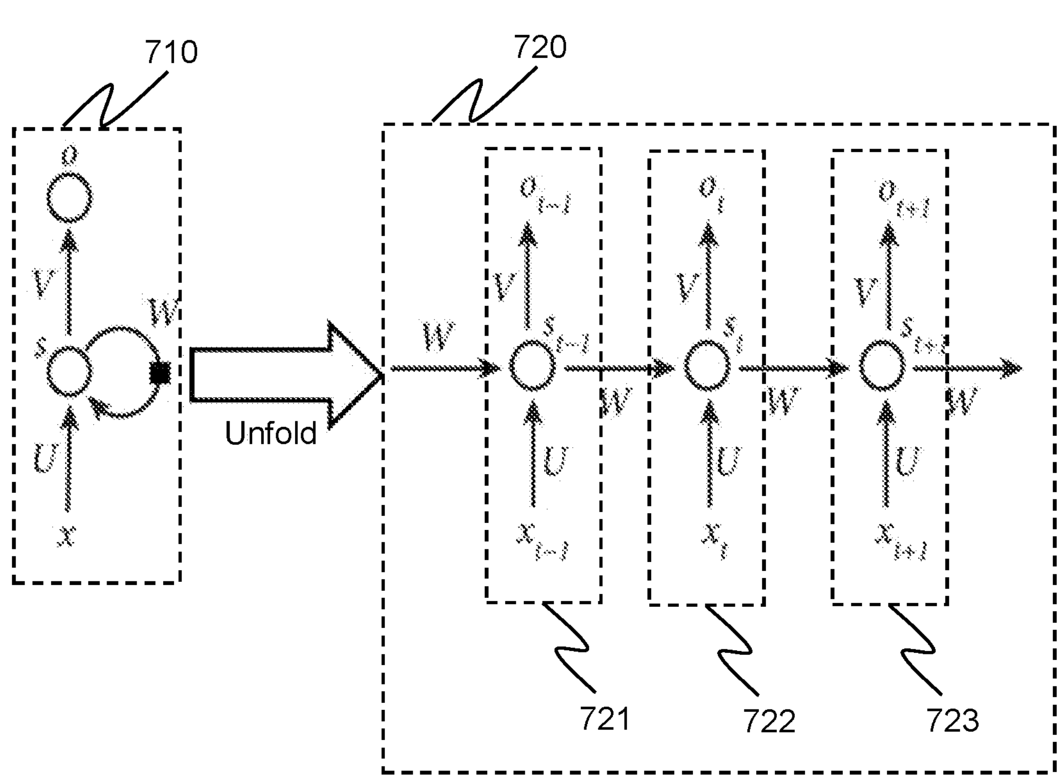
FIG. 7 illustrates an exemplary first machine learning model according to some embodiments of the present disclosure.

The first machine learning model may include an RNN model (e.g., an LSTM model), an AR model, an MA model, an ARMA model, an ARIMA model, a VAR model, an SVAR model, or the like, or any combination thereof. For illustration purposes, FIG. 7 illustrates an exemplary first machine learning model according to some embodiments of the present disclosure. As shown in FIG. 7, the first machine learning model 700 may be an LSTM model. The first machine learning model 700 may be represented as a structure 710. The structure 710 may be unfolded to a structure 720 including a plurality of sequentially connected neural networks. Each of the sequentially connected neural networks may include an input layer, a hidden layer, and an output layer. The plurality of sequentially connected neural networks may be connected by connecting their hidden layers sequentially. As shown in the structure 710, x denotes an input layer of the first machine learning model 700, s denotes a hidden layer of the first machine learning model 700, o denotes an output layer of the first machine learning model 700, W denotes a weight matrix between the plurality of sequentially connected neural networks (also referred to as matrix W), U denotes a weight matrix between the input layer and the hidden layer (also referred to as matrix U), and V denotes a weight matrix between the hidden layer and the output layer (also referred to as matrix V). That is, the matrix W may indicate a weight of an output of a previous hidden layer as an input of a current hidden layer, the matrix U may indicate a connection weight from the input layer to the hidden layer, and the matrix V may indicate a connection weight from the hidden layer to the output layer. As shown in the structure 720, the plurality of sequentially connected neural networks may include at least a neural network 721 including an input layer $x_{t-1}$, a hidden layer $s_{t-1}$, and an output layer $o_{t-1}$, a neural network 722 including an input layer $x_t$, a hidden layer $s_t$, and an output layer $o_t$, and a neural network 723 including an input layer $x_{+1}$, a hidden layer $s_{t+1}$, and an output layer $o_{t+1}$, where t denotes a time point. The neural networks 721-723 may be connected with each other by connecting the hidden layers $s_{t-1}$, $s_t$, and $s_{t+1}$. The neural network 721 may be upstream to the neural network 722. The neural network 723 may be downstream to the neural network 722. Taking the neural network 722 as an example, an input of the hidden layer $s_t$ of the neural network 722 may include an output of the hidden layer $s_{t-1}$ of the neural network 721, and an output of the hidden layer $s_t$ of the neural network 722 may be input to the hidden layer $s_{t+1}$ of the neural network 723. An input of the input layer $x_t$ of the neural network 722 may correspond to a time point (e.g., a second time point) later than a time point (e.g., a first time point) to which the input layer $x_{t-1}$ of the neural network 721 corresponds. That is, the second time point may be after the first time point.

In some embodiments, the first machine learning model 700 may include one or more model parameters. The processing device 120B may initialize parameter value(s) of the model parameter(s) before training, and one or more of the value(s) of the model parameter(s) may be updated during the training of the first machine learning model 700. Exemplary model parameters of the first machine learning model 700 may include the number (count) of the plurality of sequentially connected neural networks, a loss function, the matrix W, the matrix U, the matrix V, a training parameter of the first machine learning model 700, or the like, or any combination thereof.

In some embodiments, the training of the first machine learning model 700 may include one or more iterations. Taking a current iteration of the one or more iterations as an example, the processing device 120B may input a first sample parameter set of a sample subject (e.g., Trainning_HRrest and Trainning_HRtest) to an updated first machine learning model 700 which is obtained in a previous iteration. For example, Trainning_HRrest and Trainning_HRtest may be input to the updated first machine learning model 700 according to an equation (1):

$$\text{Input} = \text{Trainning\_HRrest} \times \text{alpha} + \text{Trainning\_HRtest} \times (1 - \text{alpha}), \quad (1)$$

where alpha denotes a training parameter of the updated first machine learning model. A value of the training parameter of the updated first machine learning model may be within a range of 0 through 1. The value of the training parameter may be set according to a default setting of the updated first machine learning model 700 or by a user. After the first sample parameter set of the sample subject is input to the updated first machine learning model 700, a heart rate curve indicating a temporal variation of the heart rate may be generated based on Trainning_HRrest and Trainning_HRtest. The heart rate curve may be input to an input layer of the updated first machine learning model 700. For example, the heart rate curve may include a plurality of heart rates over a sequence including different time points. The plurality of heart rates may be input to input layers of the plurality of neural networks of the updated first machine learning model 700 sequentially according to the sequence. Then, an output layer of the updated first machine learning model 700 may output a predicted parameter set of the sample subject (denoted as predict_HRscan). Further, the processing device 120B may determine a first assessment result which indicates an accuracy and/or efficiency of the updated first machine learning model 700.

In some embodiments, the first assessment result may be associated with a difference between predict_HRscan and HRscan. For example, the processing device 120B may determine a loss function to measure the difference. In some embodiments, the first assessment result may be associated with the number (or count) of iterations that have been performed. Additionally or alternatively, the first assessment result may be associated with the number (or count) of first training samples that have been used to train the updated first machine learning model 700. In some embodiments, the first assessment result may include a determination of whether a termination condition is satisfied in the current iteration. For example, the termination condition may be deemed satisfied if a value of the loss function is minimal or smaller than a threshold (e.g., a constant). As another example, the termination condition may be deemed satisfied if the value of the loss function converges. In some embodiments, convergence may be deemed to have occurred if, for example, the variation of values of loss functions in two or more consecutive iterations is equal to or smaller than a threshold (e.g., a constant). As still another example, the termination condition may be deemed satisfied if a certain count of iterations that have been performed. As a further example, the termination condition may be deemed satisfied if a certain count of the first training samples that have been used.

In some embodiments, in response to determining that the termination condition is satisfied in the current iteration, the processing device 120B may designate the updated first machine learning model 700 as the estimation model. In other words, parameters of the updated first machine learning model 700 may be designated as parameters of the estimation model. In response to determining that the termination condition is not satisfied, the processing device 120B may update, based on the first assessment result, parameter value(s) (e.g., values of weight matrixes such as matrix W, matrix V, or matrix U) of the updated first machine learning model 700 to be used in a next iteration. Merely by way of example, the processing device 120B may update the parameter value(s) of the updated first machine learning model 700 based on the value of the loss function according to, for example, a Backpropagation through time (BPTT) algorithm. In some embodiments, the updated first machine learning model 700 may include a plurality of parameter values, and updating parameter value(s) of the updated first machine learning model 700 refers to updating at least a portion of the parameter values of the updated first machine learning model 700.

It should be noted that the above description regarding process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, the estimation model may be stored in a storage device (e.g., the storage device 130) disclosed elsewhere in the present disclosure for further use (e.g., in the prediction of a second parameter set of a subject as described in connection with FIG. 5). As another example, after the estimation model is generated, the processing device 120B may further test the estimation model using a set of testing samples. Additionally or alternatively, the processing device 120B may update the estimation model periodically or aperiodically based on one or more newly-generated training samples (e.g., labeled third parameter set(s) as described in connection with FIG. 5).

In some embodiments, the processing device 120B may train a plurality of second machine learning models 900 corresponding to different states of a sample subject, different environments where sample scans are taken, different ranges of the heart rate of a sample subject, etc. Each of trained second machine learning models 900 may be designated as an estimation model. The training of a plurality of second machine learning models 900 can improve the training speed, the accuracy and/or the stability of the estimation model. For example, for a specific environment with a specific temperature, humidity, and air pressure, the processing device 120B may train a model A using a first portion of the first training samples associated with the specific environment. A trained model A may be designated as an estimation model corresponding to the specific environment. A sample scan in each of the first portion of the first training samples may be performed under the specific environment. As another example, for a specific state (e.g., a calm and free-breathing state, and/or a simulated scan state), the processing device 120B may train a model B using a second portion of the first training samples associated with the specific state. A first sample parameter set of a sample subject in each of the second portion of the first training samples may be acquired when the sample subject is in the specific state. A trained model B may be designated as an estimation model corresponding to the specific state. As a further example, for a specific range of the heart rate (e.g., a range of 50 beats/min~60 beats/min), the processing device 120B may train a model C using a third portion of the first training samples associated with the specific range of the heart rate. A sample subject in each of the third portion of the first training samples may have a sample range of the heart rate within the specific range of the heart rate before a sample scan is performed on the sample subject. A trained model C may be designated as an estimation model corresponding to the specific range of the hearth rate.

Figure 8:
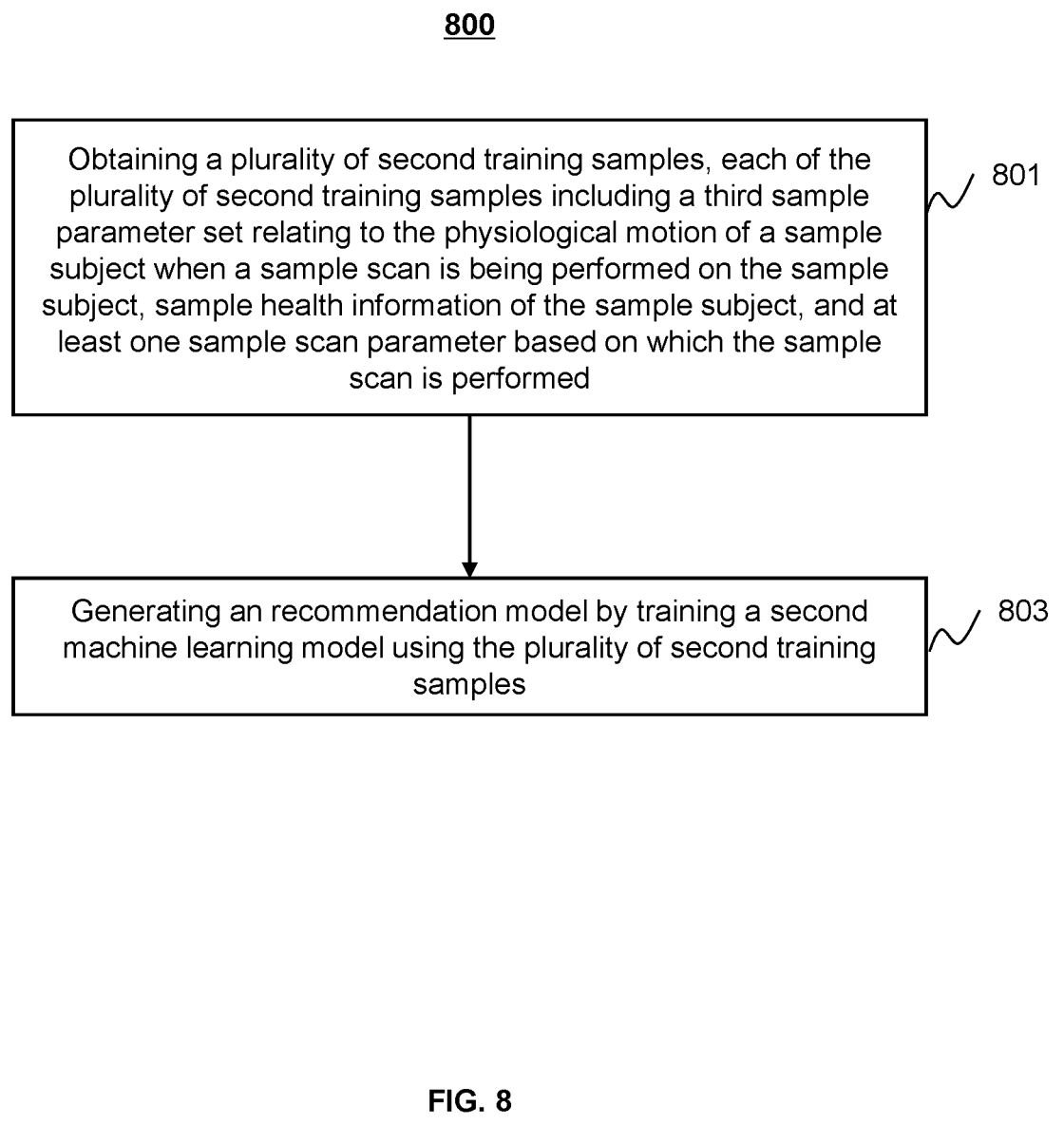

FIG. 8 is a flowchart illustrating an exemplary process for generating a recommendation model according to some embodiments of the present disclosure. In some embodiments, process 800 may be implemented as a set of instructions (e.g., an application) stored in a storage device (e.g., the storage device 130, storage 220, and/or storage 390). The processing device 120B (e.g., the processor 210, the CPU 340, and/or one or more modules illustrated in FIG. 4B) may execute the set of instructions, and when executing the instructions, the processing device 120B may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting. In some embodiments, the recommendation model described in connection with operation 505 in FIG. 5 may be obtained according to the process 800. In some embodiments, the process 800 may be performed by another device or system other than the imaging system 100, e.g., a device or system of a vendor of a manufacturer. For illustration purposes, the implementation of the process 800 by the processing device 120B is described as an example.

In 801, the processing device 120B (e.g., the obtaining module 405) may obtain a plurality of second training samples. Each of the plurality of second training samples may include a third sample parameter set relating to the physiological motion of a sample subject when a sample scan is being performed on the sample subject, sample health information of the sample subject, and at least one sample scan parameter based on which the sample scan is performed.

As used herein, a sample subject may be the same as or similar to the sample subject as described in connection with FIG. 6. In some embodiments, the sample subjects whose data are used as the second training samples may at least partially overlap the sample subjects whose data are used as the first training samples used in the training of the estimation model. In some embodiments, the sample subjects whose data are used as the second training samples may be completely different from the sample subjects whose data are used as the first training samples used in the training of the estimation model. A third sample parameter set may be the same as or similar to the second sample parameter set as described in connection with FIG. 6. The sample health information of the sample subject refers to health information of the sample subject, which is similar to the health information of the subject as described in connection with operation 505. The at least one sample scan parameter refers to ground truth scan parameter(s) for the sample scan based on which the sample scan is performed, which is similar to the adjusted at least one parameter set for the scan as described in connection with operation 507. For example, the at least one sample scan parameter may include the sample number (or count) of cardiac cycles during the sample scan, a first sample phase range during the sample scan, etc., The sample scan may be the same as or similar to the sample scan as described in connection with FIG. 6. For example, the sample scan may include a sample cardiac angiography scan. A sample image generated based on the sample scan may satisfy a clinical diagnosis need. For example, the sample image may satisfy a preset image quality.

In some embodiments, a second training sample may be previously generated and stored in a storage device (e.g., the storage device 130, the storage 220, the storage 390, or an external source). The processing device 120B may retrieve the second training sample directly from the storage device.

In 803, the processing device 120B (e.g., the training module 406) may generate the recommendation model by training a second machine learning model using the plurality of second training samples.

Figure 9:
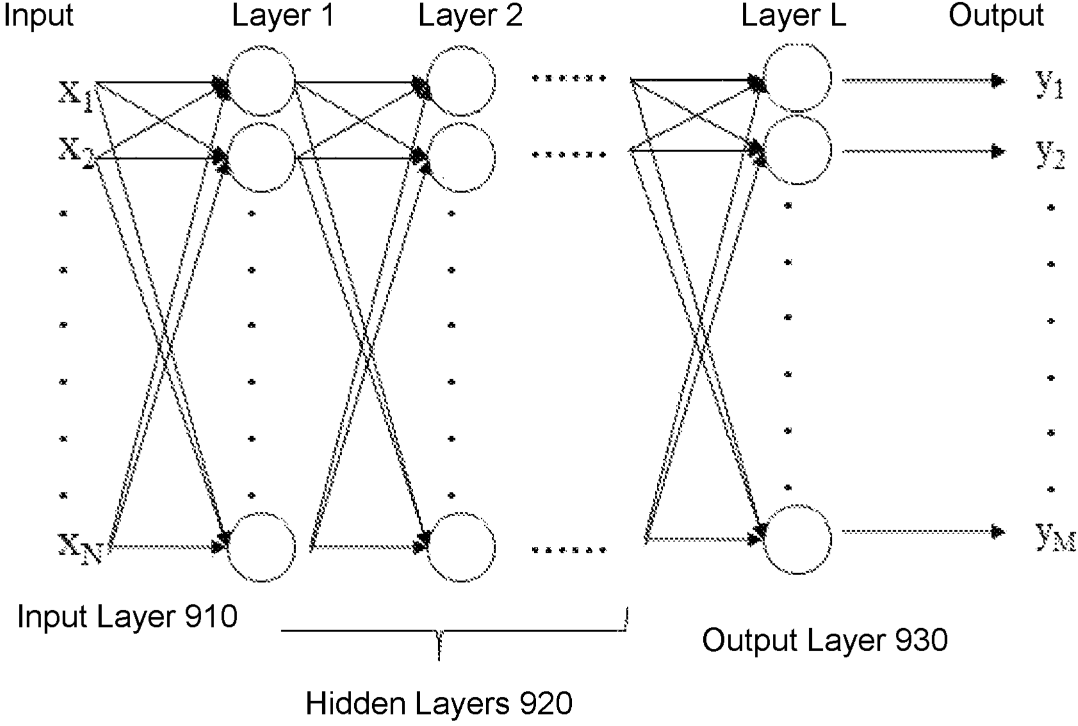
FIG. 9 illustrates an exemplary first machine learning model according to some embodiments of the present disclosure.

The second machine learning model may include an SVM model, a DT model, an RF model, a CART model, a GBDT model, an XGBoost model, a LightGBM model, a GBM model, a LASSO model, an ANN model (e.g., a CNN model), or the like, or any combination thereof. For illustration purposes, FIG. 9 illustrates an exemplary second machine learning model according to some embodiments of the present disclosure. As shown in FIG. 9, the second machine learning model 900 may be a CNN model.

The second machine learning model 900 may include an input layer 910, multiple hidden layers 920, and an output layer 930. The multiple hidden layers 920 may include one or more convolutional layers, one or more Rectified Linear Units layers (ReLU layers), one or more pooling layers, one or more fully connected layers, or the like, or a combination thereof. For example, the multiple hidden layers 920 may include a layer 1, a layer 2, . . . , a layer L. L is an integer greater than 1. Different layers of the second machine learning model 900 may perform different kinds of processing on their respective input. A successive layer may use an output from a previous layer of the successive hidden layer as an input. In some embodiments, each layer of the second machine learning model 900 may include one or more nodes (e.g., neural units). In some embodiments, each node may be connected to one or more nodes in a previous layer and/or a next layer. The number (or count) of nodes in each layer may be the same or different. In some embodiments, each node may correspond to an activation function. As used herein, an activation function of a node may define an output of the node given an input or a set of inputs. The activation function may include a sigmoid function, a tan h function, a ReLU function, an ELU function, a PRELU function, or the like, or any combination thereof. In some embodiments, the plurality of nodes may be configured to process an input of the second machine learning model 900. The input of the second machine learning model 900 may be denoted as an input vector including elements such as x1, x2, . . . , Xn. N is an integer greater than 1. In the second machine learning model 900, a node may output a value according to Equation (2) as follows:

$$f_{output} = f\left(\sum_i w_i x_i + b\right), \tag{2}$$

where $f_{output}$ denotes an output value of a node, $f(\cdot)$ denotes an activation function, $w_i$ denotes a weight corresponding to an element of an input vector, $x_i$ denotes an element of an input vector, and b denotes a bias term or vector corresponding to the input vector. Nodes in the same layer may correspond to the same bias term. That is, a specific layer may correspond to a specific bias term. Different layers may correspond to the same bias term or different bias terms. The weights and the bias terms may be parameters of the second machine learning model 900. In some embodiments, the weights and the bias terms may be iteratively updated based on a machine learning algorithm such as a stochastic gradient descent (SGD) algorithm during the training of the second machine learning model 900.

In some embodiments, the second machine learning model 900 may include one or more model parameters. The processing device 120B may initialize parameter value(s) of the model parameter(s) before training, and one or more of the value(s) of the model parameter(s) may be updated during the training of the first machine learning model 700. Exemplary model parameters of the second machine learning model 900 may include a size of a kernel of a layer, the number (or count) of layers, the number (or count) of nodes in each layer, a learning rate, a batch size, an epoch, a connected weight between two connected nodes, a bias vector relating to a node, etc. The connected weight between two connected nodes may be configured to represent a proportion of an output value of a node to be as an input value of another connected node. The bias vector relating to a node may be configured to control an output value of the node deviating from the input vector of the node.

In some embodiments, the training of the second machine learning model 900 may include one or more iterations. Taking a current iteration of the one or more iterations as an example, the processing device 120B may input the third sample parameter set and/or the sample health information of the sample subject to an updated second machine learning model 900 which is obtained in a previous iteration, and the updated second machine learning model 900 may output at least one predicted scan parameter of the sample subject. Further, the processing device 120B may determine a second assessment result which indicates an accuracy and/or efficiency of the updated second machine learning model 900.

In some embodiments, the second assessment result may be associated with a difference between the at least one predicted scan parameter and the at least one sample scan parameter. For example, the processing device 120B may determine a loss function to measure the difference. In some embodiments, the first assessment result may be associated with the number (or count) of iterations that have been performed. Additionally or alternatively, the first assessment result may be associated with the number (or count) of first training samples that have been used to train the updated second machine learning model 900. In some embodiments, the second assessment result may include a determination of whether a termination condition is satisfied in the current iteration. For example, the termination condition may be deemed satisfied if a value of the loss function is minimal or smaller than a threshold (e.g., a constant). As another example, the termination condition may be deemed satisfied if the value of the loss function converges. In some embodiments, convergence may be deemed to have occurred if, for example, the variation of values of loss functions in two or more consecutive iterations is equal to or smaller than a threshold (e.g., a constant). As still another example, the termination condition may be satisfied if a certain count of iterations that have been performed. As a further example, the termination condition may be deemed satisfied if a certain count of the first training samples that have been used.

In some embodiments, in response to determining that the termination condition is satisfied, the processing device 120B may designate the updated second machine learning model as the recommendation model. In other words, parameters of the updated second machine learning model may be designed as parameters of the recommendation model. In response to determining that the termination condition is not satisfied, the processing device 120B may update, based on the second assessment result, parameter value(s) (e.g., a value of a connected weight, a value of a bias vector) of the updated second machine learning model 900 to be used in a next iteration. Merely by way of example, the processing device 120B may update the parameter value(s) of the updated second machine learning model 900 based on the value of the loss function according to, for example, the SGD algorithm. In some embodiments, the updated second machine learning model 900 may include a plurality of parameter values, and updating parameter value (s) of the second machine learning model 900 refers to updating at least a portion of the parameter values of the updated second machine learning model 900.

In some embodiments, the processing device 120B may train a plurality of second machine learning models 900, respectively, each of which corresponds to a subset of the at least one sample scan parameter. That is, for each of the second machine learning models 900, an input of the second machine learning model 900 may be the third sample parameter set and/or the sample health information of the sample subject, and an output of the second machine learning model 900 may be a subset of predicted scan parameter (s) of at least one sample scan parameter. A subset of the at least one sample scan parameter may include one or more parameters.

For example, the processing device 120B may train a first model corresponding to the sample number (or count) of cardiac cycles during the sample scan. In such occasions, an input of the first model may include the third sample parameter set and/or the sample health information of the sample subject, and an output of the first model may include a predicted count of cardiac cycles (e.g., an integer within a range of 1 through 5) during the sample scan. The processing device 120B may update the first model based at least in part on the predicted count of cardiac cycles and the sample count of cardiac cycles according to a machine learning algorithm as described elsewhere in the present disclosure.

As another example, the processing device 120B may train a second model corresponding to the first sample phase range during the sample scan. The first sample phase range during the sample scan refers to a certain phase range within a cardiac cycle during which scan data (e.g., image data) is acquired when the sample scan is performed on the sample subject. In such occasions, an input of the second model may include the third sample parameter set and/or the sample health information of the sample subject, and an output of the second model may include a first predicted phase range. The first predicted phase range may be within a range of 0 through 1, a precision of which is 0.01. That is, a value in the first predicted phase range may be accurate to two decimal places. For instance, the predicted phase range may be represented as 0.25~0.65 (i.e., 25%~65%), 0.30~0.70 (i.e., 30%~70%), etc. The smaller the precision is, the more accurate the first predicted phase range may be. In some embodiments, the first predicted phase range may be denoted as a vector A with a length of 100, i.e., including 100 elements. For example, if the first predicted phase range is 30%~60%, values from the 30th element to the 60th element of a corresponding vector A may be 1, and values of the remaining elements of the corresponding vector A may be 0. The processing device 120B may update the second model based at least in part on the first predicted phase range and the first sample phase range for the sample scan according to a machine learning algorithm as described elsewhere in the present disclosure. In some embodiments, the processing device 120B may combine a plurality of trained second machine learning models 900 (e.g., a trained first model and a trained second model) to generate the recommendation model.

In some embodiments, the plurality of second training samples (or a portion thereof) may need to be preprocessed before being used in training the second machine learning model 900. For example, for a second training sample, the processing device 120B may preprocess sample health information of a sample subject in the second training sample. For example, the processing device 120B may perform a word segmentation operation on the sample health information. As used herein, the word segmentation operation refers to an operation to process text including, e.g., a character, an English word, a number, or the like, or a combination thereof, to facilitate human-computer interaction. Taking the sample health information including a string of words as an example, the word segmentation operation may include removing non-text parts (e.g., spaces), stop words (e.g., "a," "to," etc.), etc., to remove irrelevant or nonsignificant information in the sample health information of a second training sample. The word segmentation operation may include converting a capital character in the sample health information to a lowercase character. The word segmentation operation may also include a model such as a Bag of Words model, an N-gram language model, or a Word2vec distributed model to segment words in the sample health information expressed in Chinese. For instance, the processing device 120B may preprocess the sample health information using the Word2vec model. The preprocessed sample health information may be expressed in the form of a vector. Specifically, the processing device 120B may create a dictionary containing all words each of which has a unique number or identification in the dictionary. Any word can be represented by an N-dimensional one-hot vector.

By the preprocessing process with vectorization, the processing device 120B may transform an original input (e.g., the age of a sample subject, the gender of the sample subject, the BMI of the sample subject, a medication that the sample subject has been or is taking, information associated with a scanned portion of the sample subject, information relating to an injection of a contrast agent injected to the sample subject, information of a goal of diagnosis and treatment of the sample subject, etc.) of the second machine learning model 900 into a high-dimensional and sparse vector. The processing device 120B may further transform the high-dimensional and sparse vector into a low-dimensional and dense vector using a dimensionality reduction algorithm so as to input to the second machine learning model. The dimensionality reduction algorithm may include a missing value ratio algorithm, a low variance filtering algorithm, a high correlation filtering algorithm, a principal component analysis algorithm, a reverse feature elimination algorithm, a previous feature construction algorithm, or the like, or any combination thereof.

In some embodiments, the second training samples (or a portion thereof) may be preprocessed and stored in a storage device (e.g., the storage device 130, the storage 220, the storage 390, or an external source). For example, sample health information of a second training sample may have been preprocessed and stored in the storage device. The processing device 120B may retrieve the second training sample from the storage device, and apply the second training sample in training the second machine learning model 900 without preprocessing the second training sample.

It should be noted that the above description regarding process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, the recommendation model may be stored in a storage device (e.g., the storage device 130) disclosed elsewhere in the present disclosure for further use (e.g., in determining the at least one scan parameter as described in connection with FIG. 5). As another example, after the recommendation model is generated, the processing device 120B may further test the recommendation model using a set of testing images. Additionally or alternatively, the processing device 120B may update the recommendation model periodically or aperiodically based on one or more newly-generated training samples (e.g., labeled adjusted scan parameter as described in connection with FIG. 5). In some embodiments, the second machine learning model 900 may be trained jointly with the first machine learning model 700 to generate a single trained model. During an application, an input of the single trained model may include a first parameter set of the subject and health information of the subject, and an output of the single trained model may include at least one scan parameter for a scan to be performed on the subject.

In some embodiments, a second training sample may further include additional features including a sample characteristic of an operator (e.g., a doctor or technician operating a medical device to perform the sample scan on the sample subject), the image quality of a sample image generated based on the sample scan, an image type of the sample scan, a sample type of the medical device, etc. During the training process, the additional features may be input to the second machine learning model 900 with the third sample parameter set and/or the sample health information to generate a second predicted at least one scan parameter. The processing device 120B may update the second machine learning model 900 based on the second predicted at least one scan parameter and the at least one sample scan parameter according to a machine learning algorithm as disclosed elsewhere in the present disclosure.

In some embodiments, during the training process, the processing device 120B may train a plurality of second machine learning models 900 corresponding to different sample product information of medical devices, different sample types of medical devices, different goals of diagnosis and treatment of sample subjects, different pre-existing conditions of sample subjects, etc. Each of trained second machine learning models 900 may be designated as a recommendation model. The training of the plurality of second machine learning models 900 can improve the training speed, the accuracy, and/or the stability of the recommendation model. For example, for a specific type of medical device, the processing device 120B may train a model 1 using a first portion of the second training samples associated with the specific type medical device. A sample scan in the first portion of the second training samples may be performed using the specific type of medical device. A trained model 1 may be designated as a recommendation model corresponding to the specific type of medical device. As another example, for a specific goal of an assessment of coronary stenosis, the processing device 120B may train a model 2 using a second portion of the second training samples associated with the specific goal. A sample scan in the second portion of the second training samples may be performed for the specific goal. A trained model 2 may be designated as a recommendation model corresponding to the specific goal. As a further example, for a pre-existing condition, the processing device 120B may train a model 3 using a third portion of the second training samples from sample subjects who have the pre-existing condition. A trained model 3 may be designated as a recommendation model corresponding to the pre-existing condition.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (Saas).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for scan preparation, comprising:

a medical device configured to perform the scan;

at least one storage device including a set of instructions; and at least one processor configured to communicate with the at least one storage device, wherein when executing the set of instructions, the at least one processor is configured to direct the system to perform operations including:

obtaining at least one default scan parameter for the scan;

obtaining a first parameter set of a subject to be scanned by the medical device acquired before the scan is performed on the subject, the first parameter set relating to a physiological motion of the subject acquired before the scan is performed on the subject, wherein the first parameter set includes at least one of a first parameter sub-set acquired when the subject is not undergoing any scan and a second parameter sub-set acquired when the subject is undergoing a simulated scan;

inputting the first parameter set to an estimation model to output a second parameter set of the subject by the estimation model, the second parameter set relating to the physiological motion of the subject;

automatically determining at least one scan parameter for the scan based at least in part on the second parameter set output by the estimation model;

performing, by the medical device, the scan on the subject based on the at least one scan parameter, including:

adjusting the at least one default scan parameter according to the at least one scan parameter determined based on the outputted second parameter set of the estimation model; and performing, by the medical device, the scan on the subject based on the at least one adjusted scan parameter; and generating an image according to the scan.

2. The system of claim 1, wherein the inputting of the estimation model further includes health information of the subject.

3. The system of claim 1, wherein the estimation model is a trained machine learning model, the estimation model is generated by a processing including:

obtaining a plurality of first training samples, each of the plurality of first training samples including a first sample parameter set relating to the physiological motion of a sample subject acquired before a sample scan is performed on the sample subject and a second sample parameter set relating to the physiological motion of the sample subject acquired when the sample scan is being performed on the sample subject; and generating the estimation model by training a first machine learning model using the first plurality of training samples.

4. The system of claim 3, wherein the each of the plurality of first training samples includes sample health information of the sample subject.

5. The system of claim 1, wherein the first parameter sub-set is acquired during a first time period, the second parameter sub-set is acquired during a second time period different from the first time period, the first parameter set is obtained by one or more detection devices, and the one or more detection devices include an ECG monitor or a wearable device.

6. The system of claim 5, wherein the subject is not undergoing any scan during the first time period, and the subject is undergoing the simulated scan during the second time period.

7. The system of claim 1, wherein the predicting, based on the first parameter set and an estimation model, a second parameter set of the subject includes:

predicting the second parameter set of the subject by inputting the first parameter set to the estimation model.

8. The system of claim 1, wherein the determining at least one scan parameter for the scan based at least in part on the second parameter set includes:

obtaining a recommendation model;

obtaining health information of the subject; and determining the at least one scan parameter for the scan by inputting the second parameter set and the health information of the subject into the recommendation model.

9. The system of claim 8, wherein the inputting the second parameter set and the health information of the subject into the recommendation model includes:

preprocessing the health information of the subject; and inputting the second parameter set and the preprocessed information of the subject into the recommendation model.

10. The system of claim 9, wherein the preprocessing the health information of the subject includes:

performing a word segmentation operation on the health information of the subject.

11. The system of claim 1, wherein the at least one processor is further configured to direct the system to perform the operations including:

causing at least a portion of the at least one scan parameter to be presented to a user; and after the generating the image according to the scan, displaying the image on an interface of a terminal.

12. The system of claim 11, wherein the at least one processor is further configured to direct the system to perform the operations including receiving a user input, and the causing the medical device to perform the scan on the subject based on the at least one scan parameter includes:

causing the medical device to perform the scan on the subject based on the at least one scan parameter and the user input.

13. The system of claim 12, wherein the causing the medical device to perform the scan on the subject based on the at least one scan parameter and the user input includes:

adjusting the at least one scan parameter based on the user input; and causing the medical device to perform the scan on the subject based on the adjusted at least one scan parameter.

14. The system of claim 13, wherein the at least one processor is further configured to direct the system to perform the operations including:

adjusting the at least one scan parameter until an image generated by the scan performed on the subject based on the adjusted at least one scan parameter satisfies a preset condition.

15. The system of claim 14, wherein the at least one processor is further configured to direct the system to perform the operations including:

updating a recommendation model based at least in part on the second parameter set, health information of the subject, and the adjusted at least one scan parameter, the recommendation model being configured to determine the at least one scan parameter for the scan.

16. The system of claim 1, wherein the at least one processor is further configured to direct the system to perform the operations including:

obtaining a third parameter set of the subject acquired when the scan is being performed on the subject;

determining a difference between the third parameter set of the subject and the second parameter set of the subject; and determining whether to update the estimation model based at least in part on the difference.

17. The system of claim 1, wherein the scan is associated with a cardiac angiography, the physiological motion includes cardiac motion of the subject, and the first parameter set or the second parameter set relates to a heart rate of the subject.

18. A method for scan preparation, implemented on a medical device and a computing device including at least one processor and at least one storage device, the method comprising:

obtaining a first parameter set of a subject to be scanned by a medical device acquired before a scan is performed on the subject, the first parameter set relating to a physiological motion of the subject acquired before the scan is performed on the subject, wherein the first parameter set includes at least one of a first parameter sub-set acquired when the subject is not undergoing any scan and a second parameter sub-set acquired when the subject is undergoing a simulated scan;

inputting the first parameter set to an estimation model to output a second parameter set of the subject by the estimation model, the second parameter set relating to the physiological motion of the subject;

automatically determining at least one scan parameter for the scan based at least in part on the second parameter set output by the estimation model, including:

obtaining a recommendation model; and determining the at least one scan parameter for the scan by inputting the second parameter set into the recommendation model;

performing, by the medical device, the scan on the subject based on the at least one scan parameter; and generating an image according to the scan.

19. A non-transitory computer readable medium, comprising executable instructions that, when executed by at least processor, direct a medical device and the at least one processor to perform a method for scan preparation, the method comprising:

obtaining a first parameter set of a subject to be scanned by a medical device acquired before a scan is performed on the subject, the first parameter set relating to a physiological motion of the subject acquired before the scan is performed on the subject, wherein the first parameter set includes at least one of a first parameter sub-set acquired when the subject is not undergoing any scan and a second parameter sub-set acquired when the subject is undergoing a simulated scan;

inputting the first parameter set to an estimation model to output a second parameter set of the subject by the estimation model, the second parameter set relating to the physiological motion of the subject, the estimation model being a trained machine learning model, the trained machine learning model being trained using a plurality of training samples;

automatically determining at least one scan parameter for the scan based at least in part on the second parameter set output by the estimation model;

performing, by the medical device, the scan on the subject based on the at least one scan parameter; and generating an image according to the scan.

* * * * *